(12) United States Patent
Hazan et al.

(10) Patent No.: US 10,159,680 B2
(45) Date of Patent: *Dec. 25, 2018

(54) COMPOSITIONS COMPRISING ACIDIC EXTRACTS OF MASTIC GUM

(71) Applicant: REGENERA PHARMA LTD., Rehovot (IL)

(72) Inventors: Zadik Hazan, Zichron Yaakov (IL); Andre C. B. Lucassen, Rehovot (IL)

(73) Assignee: REGENERA PHARMA LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/677,365

(22) Filed: Aug. 15, 2017

(65) Prior Publication Data

US 2017/0368076 A1   Dec. 28, 2017

Related U.S. Application Data

(62) Division of application No. 15/000,849, filed on Jan. 19, 2016, now Pat. No. 9,770,456, which is a division of application No. 13/821,194, filed as application No. PCT/IL2011/000724 on Sep. 7, 2011, now Pat. No. 9,271,949.

(60) Provisional application No. 61/380,339, filed on Sep. 7, 2010.

(51) Int. Cl.
| | | |
|---|---|---|
| *A61K 31/569* | (2006.01) | |
| *A61K 36/22* | (2006.01) | |
| *A61K 31/57* | (2006.01) | |
| *A61K 31/19* | (2006.01) | |

(52) U.S. Cl.
CPC ............ *A61K 31/569* (2013.01); *A61K 31/19* (2013.01); *A61K 31/57* (2013.01); *A61K 36/22* (2013.01); *A61K 2236/39* (2013.01); *C12N 2501/999* (2013.01); *C12N 2506/00* (2013.01)

(58) Field of Classification Search
CPC ...... A61K 31/569; A61K 31/56; A61K 36/22; C12N 2506/00; C12N 2501/00; C12N 2501/999

See application file for complete search history.

(56) References Cited

U.S. PATENT DOCUMENTS

| | | | |
|---|---|---|---|
| 4,713,243 A | 12/1987 | Schiraldi | |
| 5,637,290 A | 6/1997 | Sodis | |
| 5,948,430 A | 9/1999 | Zerbe | |
| 6,074,688 A | 6/2000 | Pletcher | |
| 6,177,096 B1 | 1/2001 | Zerbe | |
| 6,207,403 B1 | 3/2001 | Goldstein | |
| 6,284,264 B1 | 9/2001 | Zerbe | |
| 6,319,541 B1 | 11/2001 | Pletcher | |
| 6,592,887 B2 | 7/2003 | Zerbe | |
| 6,623,728 B2 | 9/2003 | Harichian | |
| 6,709,671 B2 | 3/2004 | Zerbe | |
| 6,811,769 B2 | 11/2004 | Watanabe | |
| 7,048,943 B2 | 5/2006 | Barenholz | |
| 7,268,124 B2 | 9/2007 | Wiemer | |
| 7,294,651 B2 | 11/2007 | Syverson | |
| 7,358,377 B2 | 4/2008 | Wiemer | |
| 8,722,105 B2 | 5/2014 | Hazan | |
| 8,956,601 B2 | 2/2015 | Hazan | |
| 9,271,949 B2 | 3/2016 | Hazan | |
| 9,770,456 B2 * | 9/2017 | Hazan | .................. A61K 31/569 |
| 2005/0238740 A1 | 10/2005 | Fotinos | |
| 2007/0249543 A1 | 10/2007 | Zadini | |
| 2009/0048205 A1 | 2/2009 | Meyer | |
| 2014/0294928 A1 | 10/2014 | Hazan | |

FOREIGN PATENT DOCUMENTS

| | | |
|---|---|---|
| CN | 1173134 | 2/1998 |
| EP | 1520585 | 4/2005 |
| GR | 1003541 | 3/2001 |
| GR | 1003868 | 4/2002 |
| JP | 2007135493 | 6/2007 |
| WO | 01/21212 | 3/2001 |
| WO | 03/092712 | 11/2003 |
| WO | 03/097212 | 11/2003 |
| WO | 2005/094837 | 10/2005 |
| WO | 2005/112967 | 12/2005 |
| WO | 2006/003659 | 1/2006 |
| WO | 2008/024374 | 2/2008 |
| WO | 2010/030082 | 3/2010 |
| WO | 2010/100650 | 9/2010 |
| WO | 2010/100651 | 9/2010 |

OTHER PUBLICATIONS

Al-Habbal et al., (1984) A double-blind controlled clinical trial of mastic and placebo in the treatment of duodenal ulcer. Clin Exp Pharmacol Physiol 11 (5): 541-4.
Al-Said et al., (1986) Evaluation of mastic, a crude drug obtained from Pistacia lentiscus for gastric and duodenal anti-ulcer activity. J Ethnopharmacol 15(3): 271-8.
Andrikopoulos et al., (2003) Biological activity of some naturally occurring resins, gums and pigments against in vitro LDL oxidation. Phytother Res 17(5): 501-7.
Arrieta et al., (2003) Purification of gastroprotective triterpenoids from the stem bark of Amphipterygium adstringens; role of prostaglandins, sulfhydryls, nitric oxide and capsaicin-sensitive neurons. Planta Med 69(10): 905-9.
Atmani et al., (2009) Antioxidant capacity and phenol content of selected Algerian medicinal plants. Food Chem 112 (2): 303-309.
Barra et al., (2007) Characterization of the Volatile Constituents in the Essential Oil of Pistacia lentiscus L. from Different Origins and Its Antifungal and Antioxidant Activity. J Agric Food Chem 55(17): 7093-7098.
Barton and Seoane (1956) 801. Triterpenoids. Part XXII. The constitution and stereochemistry of masticadienonic acid. J Chem Soc 1956: 4150-4157.
Bebb et al., (2003) Mastic gum has no effect on Helicobacter pylori load in vivo. J Antimicrob Chemother 52(3): 522-523.

(Continued)

*Primary Examiner* — Theodore R. West
(74) *Attorney, Agent, or Firm* — Rothwell, Figg, Ernst & Manbeck, P.C.

(57) ABSTRACT

The invention relates to compositions and formulations comprising isolated acidic fraction of mastic gum and uses thereof for treating impaired neurological functions as well as wound and tissue repair.

12 Claims, 27 Drawing Sheets

(56) References Cited

OTHER PUBLICATIONS

Boudsocq et al., (2005) Modulation of cellular response to cisplatin by a novel inhibitor of DNA polymerase beta. Mol Pharmacol 67(5): 1485-92.

Chávez et al., (2005) Cytotoxic activity and effect on nitric oxide production of tirucallane-type triterpenes. J Pharm Pharmacol 57(9): 1087-91.

Dietemann et al., (2000) Artificial Photoaging of Triterpenes Studied by Graphite-Assisted Laser Desorption/Ionization Mass Spectrometry. Helv Chim Acta 83: 1766.

Dietemann et al., (2005) Chios gum mastic e freshly harvested vs. commercial resin and its implications to aging of tarnishes, Zeitschrift fur Kunsttechnologie and Konservierung 19: 119-130.

Giner-Larza et al., (2002) Anti-inflammatory triterpenes from Pistacia terebinthus galls. Planta Med 68(4): 311-315.

Kaliora et al., (2004) Detection and Identification of Simple Phenolics in Pistacia lentiscus Resin. Journal of Liquid Chromatography & Related Technologies 27(2): 289-300.

Keisari (1992) colorimetric microtiter assay for the quantitation of cytokine activity on adherent cells in tissue culture. J Immunol Methods 146(2): 155-161.

Ljungman (2009) Targeting the DNA Damage Response in Cancer. Chem Rev 109 (7): 2929-2950.

Loughlin et al., (2003) Monotherapy with mastic does not eradicate Helicobacter pylori infection from mice. J Antimicrob Chemother 51(2): 367-371.

Mansouri et al., (2005) The effect of Pistacia vera L. gum extract on oxidative damage during experimental cerebral ischemia-reperfusion in rats. Iranian Biomedical Journal 9(4): 181-185.

Marner et al., (1991) Triterpenoids from gum mastic, the resin of Pistacia lentiscus. Phytochemistry 30(11): 3709-3712.

Marone et al., (2001) Bactericidal activity of Pistacia lentiscus mastic gum against Helicobacter pylori. J Chemother (6): 611-4.

Modugno et al., (2006) Chemical study of triterpenoid resinous materials in archaeological findings by means of direct exposure electron ionisation mass spectrometry and gas chromatography/mass spectrometry. Rapid Commun Mass Spectrom 20(11): 1787-800.

Olivera Ortega et al., (1999) Phytochemical study of cuachalalate (Amphiptherygium adstringens, Schiede ex Schlecht). J Ethnopharmacol 68(1-3): 109-13.

Oviedo-Chávez et al., (2004) Principles of the bark of Amphipterygium adstringens (Julianaceae) with anti-inflammatory activity. Phytomedicine 11(5): 436-45.

Papageorgiou et al., (1997) Gas chromatographic—mass spectroscopic analysis of the acidic triterpenic fraction of mastic gum. Journal of Chromatography A 769(2): 263-273.

Paraschos et al., (2007) In Vitro and In Vivo Activities of Chios Mastic Gum Extracts and Constituents against Helicobacter pylori. Antimicrob Agents Chemother 51(2): 551-559.

Sharifi and Hazell (2009) Fractionation of Mastic Gum in Relation to Antimicrobial Activity. Pharmaceuticals 2: 2-10.

Van den Berg et al., (1998) Cis-1,4-poly-β-myrcene; the structure of the polymeric fraction of mastic resin (Pistacia lentiscus L.) elucidated. Tetrahedron Letters 39(17): 2645-2648.

Yueqin et al., (2003) Isolation of two triterpenoids and a biflavanone with anti-Inflammatory activity from *Schinus molle* fruits. Planta Med 69(10): 893-8.

CAS Registry record for "Masticadienoic Acid" (retrieved Aug. 2014).

Caputo et al., (1975) Triterpenes of galls of Pist acia terebinthus: Galls produced by Pemphigus utricularius. Phytochemistry 14(3): 809-811.

Caputo et al., (1978) Triterpenes from the bled resin of Pistacia vera. Phytochemistry 17(4): 815-817.

Caputo et al., (1979) Triterpenes from the galls of Pistacia palestina. Phytochemistry 18(5): 896-898.

\* cited by examiner

03-JUN-2010

TOF MS

REGENERA2 234 (4.337)AM(CEN,4,80.00,Ht.5000.0,0.00,0.70);Cm(213:292−20:178x5.000)

| NO: | MASS: | INTEN | %BPI | %TIC | NO: | MASS: | INTEN | %BPI | %TIC |
|---|---|---|---|---|---|---|---|---|---|
| 1: | 409 | 3.01e1 | 2.42 | 0.58 | | | | | |
| 2: | 437 | 3.40e1 | 2.74 | 0.65 | | | | | |
| 3: | 437 | 2.33e2 | 18.73 | 4.46 | | | | | |
| 4: | 438 | 5.26e1 | 4.24 | 1.01 | | | | | |
| 5: | 439 | 4.89e1 | 3.94 | 0.94 | | | | | |
| 6: | 455 | 3.50e1 | 2.82 | 0.67 | | | | | |
| 7: | 455 | 1.24e3 | 100.00 | 23.83 | | | | | |
| 8: | 456 | 7.40e1 | 5.95 | 1.42 | | | | | |
| 9: | 456 | 3.00e2 | 24.12 | 5.75 | | | | | |
| 10: | 469 | 1.02e2 | 8.22 | 1.96 | | | | | |
| 11: | 471 | 4.10e1 | 3.30 | 0.79 | | | | | |
| 12: | 474 | 2.20e1 | 1.77 | 0.42 | | | | | |
| 13: | 477 | 5.01e2 | 42.75 | 10.19 | | | | | |
| 14: | 491 | 4.24e1 | 3.41 | 0.81 | | | | | |
| 15: | 493 | 1.24e1 | 1.00 | 0.24 | | | | | |
| 16: | 518 | 9.26e1 | 7.45 | 1.78 | | | | | |
| 17: | 691 | 4.67e1 | 3.76 | 0.90 | | | | | |
| 18: | 691 | 5.40e1 | 4.34 | 1.04 | | | | | |
| 19: | 691 | 4.00e0 | 0.82 | 0.08 | | | | | |
| 20: | 702 | 2.00e1 | 1.61 | 0.38 | | | | | |
| 21: | 705 | 4.68e1 | 3.77 | 0.90 | | | | | |
| 22: | 705 | 8.56e1 | 6.88 | 1.64 | | | | | |
| 23: | 705 | 4.15e1 | 3.34 | 0.80 | | | | | |
| 24: | 705 | 3.93e1 | 3.17 | 0.75 | | | | | |
| 25: | 910 | 4.37e2 | 35.12 | 8.37 | | | | | |
| 26: | 910 | 1.73e2 | 13.92 | 3.32 | | | | | |
| 27: | 910 | 4.50e1 | 3.62 | 0.86 | | | | | |
| 28: | 911 | 2.20e2 | 17.73 | 4.23 | | | | | |
| 29: | 911 | 4.20e1 | 3.38 | 0.61 | | | | | |
| 30: | 912 | 700e0 | 0.56 | 0.13 | | | | | |
| 31: | 912 | 1.08e2 | 8.68 | 2.07 | | | | | |
| 32: | 913 | 1.37e1 | 1.10 | 0.26 | | | | | |
| 33: | 924 | 1.49e1 | 1.20 | 0.29 | | | | | |
| 34: | 932 | 3.55e2 | 28.59 | 6.81 | | | | | |
| 35: | 932 | 3.02e2 | 24.30 | 5.79 | | | | | |
| 36: | 932 | 3.42e1 | 2.75 | 0.68 | | | | | |
| 37: | 933 | 2.18e2 | 17.52 | 4.18 | | | | | |
| 38: | 948 | 1.35e1 | 1.09 | 0.26 | | | | | |

FIG.3B

COMPOSITIONS COMPRISING ACIDIC EXTRACTS OF MASTIC GUM

CROSS REFERENCE TO RELATED APPLICATIONS

The present application is a divisional of U.S. patent application Ser. No. 15/000,849, filed on Jan. 19, 2016, now U.S. Pat. No. 9,770,456 issued on Sep. 26, 2017, which is a divisional of U.S. patent application Ser. No. 13/821,194, filed on Mar. 6, 2013, now U.S. Pat. No. 9,271,949 issued on Mar. 1, 2016, which is a 35 U.S.C. § 371 National Phase Entry Application from PCT/IL2011/000724 filed on Sep. 7, 2011, which claims priority under 35 U.S.C. § 119 to U.S. Provisional Patent Application No. 61/380,339 filed on Sep. 7, 2010, which are incorporated herein by reference in their entireties.

FIELD OF THE INVENTION

The invention relates to compositions of isolated acidic fractions from mastic gum, and uses thereof.

BACKGROUND OF THE INVENTION

The pursuit of new drug entities derived from plants and plant products for various therapeutic applications has its origins in antiquity and continues to the present. One such source is mastic, also known as gum mastic or mastic gum, which is a tree resin obtained as an exudate from *Pistacia lentiscus* L., a member of the family Anacardiaceae. Mastic was used in the ancient Mediterranean world for gastrointestinal disorders such as gastralgia, dyspepsia and peptic ulcer. Oral administration of mastic to human patients with duodenal ulcer and to experimental rats with induced gastric and duodenal ulcers has been disclosed to have therapeutic effects (Al-Habbal et al (1984) Clin Exp Pharmacop Physio 11(5):541-4; Said et al (1986) J Ethnopharmacol 15(3):271-8). While it has been disclosed that mastic has in vitro bactericidal effects against *Helicobacter pylori*, the etiologic agent causing peptide ulcer disease (Marone et al (2001) J Chemother 13:611-614), other reports disclose that mastic does not exert anti-bacterial activity upon administration to *H. pylori* positive human patients (Bebb et al (2003) J Antimicrob Chemother 52:522-23) or to experimentally infected mice (Loughlin et al (2003) J Antimicrob Chemother 51:367-371).

Greek Patent No. GR 1,003,541 discloses antimicrobial and antifungal action of the chios mastic oil extracted from the leaves, branches and fruit of *Pistacia lentiscus* var Chia.

Greek Patent No. GR 1,003,868 discloses use of a product derived from *Pistacia lentiscus* var. Chia as an antioxidant, as a wound healing inductor and as a cytostatic agent.

U.S. Patent Application Publication No 2005/0238740 is directed to Use of mastic and its components for the control of microbial infections.

Paraschos et al (2007), authored by some of the inventors of the aforementioned patent application, disclose preparation of a total mastic extract without polymer (TMEWP), prepared by polar solvent extraction of crude mastic and removal of the insoluble polymer poly-β-myrcene therefrom, and acidic and neutral fractions separated from TMEWP (Paraschos et al (2007) Antimicrob Agents Chemother 51(2):551-559). According to the disclosure, administration of TMEWP to *H. pylori* infected mice over a period of 3 months resulted in a 30-fold reduction of bacterial colonization, largely attributable to a particular compound purified from the acid fraction. The authors indicate that TMEWP was prepared since the high percentage of poly-β-myrcene in crude mastic preparations, as used in previous studies, was speculated to hinder potential in vivo activity during oral administration. The authors further disclose that removal of the poly-β-myrcene can produce an enhanced therapeutic moiety with anti-*H. pylori* activity.

EP Patent Application No. 1520585 is directed to Cancer treatment using natural plant products or essential oils or components from some *pistacia* species.

International Patent Application Publication No. WO 2005/112967 is directed to anticancer activity of chios mastic gum.

Van der Berg et al (1998) disclose isolation and purification of the polymer fraction of mastic using extraction and size exclusion chromatography (Van der Berg et al (1998) Tetrahedron Lett 3:2645-2648).

Barra et al (2007) disclose extraction and gas chromatographic analysis of essential oil from *P. lentiscus* L. (Barra et al (2007) J Agric Food Chem 55(17):7093-7098). According to the disclosure, a total of 45 compounds were identified, including β-myrcene as one of the major compounds.

International Patent Application Publication No. WO 2010/100650 to some of the inventors of the present invention, is directed to therapeutic uses of mastic gum fractions.

International Patent Application Publication No. WO 2010/100651 to some of the inventors of the present invention, is directed to compositions of polymeric myrcene.

International Patent Application Publication No. WO 2005/094837 is directed to Use of masticadienoic acid as inhibitor of DNA polymerase-beta, used for treating cancers, tumors and neurodegenerative diseases.

Marner et al (1991) disclose identification of various triterpenoids from gum mastic of *P. lentiscus* (Marner et al (1991) Phytochemistry, 30, 3709-3712).

Giner-Larza et al (2002) disclose anti-inflammatory triterpenes from *pistacia* terebinthus galls (Planta Med (2002), 68, 311-315).

Nevertheless, there remains an unmet need for safe, versatile and effective agents for treatment of various conditions, such as those associate with impaired neurological functions and related neurodegenerative conditions, including, for example, Alzheimer's disease, stroke, and the like, as well and other conditions, such as tissue regeneration, wound and tissue repair.

SUMMARY OF THE INVENTION

The present invention provides pharmaceutical compositions comprising an isolated acidic fraction of mastic gum, which contains acidic compounds that are soluble in both polar and non-polar organic solvents. The fraction of the invention exhibits a variety of beneficial biological activities which may be exploited for various therapeutic applications. More specifically, an isolated acidic fraction of mastic gum is now disclosed to have activity and be useful in treating impaired neurological functions and related neurodegenerative conditions (for example, by reversal of the neurodegenerative condition), stroke, tissue regeneration, wound and tissue repair, and the like.

According to some embodiments, the present invention further provides compositions comprising isolated compounds from the isolated acidic fraction of mastic gum, having therapeutic activity. In some embodiments, the compositions may include a plurality of isolated compounds selected from the individual acidic compounds found in the acidic fraction of mastic gum according to the invention. According to some embodiments the composition includes at least three isolated compounds selected from masticadienoic acid, isomasticadienoic acid, masticadienolic acid, isomasticadienolic acid, 3-O-acetyl masticadienolic acid, 3-O-acetyl epimasticadienolic acid, 3-O-acetyl isomasticadienolic acid, 3-O-acetyl epi-isomasticadienolic acid, oleanonic acid, moronic acid and 3-oxo-lup-20(29)-en-28-oic acid. In some exemplary embodiments, the compositions include at least masticadienoic acid, isomasticadienoic acid and oleanonic acid. Such compositions unexpectedly exhibit a synergistic effect, whereby the combination of compounds exhibit a markedly improved therapeutic effect in the treatment of impaired neurological functions and neurodegenerative disorders/conditions, as compared to the individual compounds alone.

The mastic acidic fraction according to embodiments of the invention may be distinguished over mastic fractions disclosed in the prior art, as its preparation involves use of both a polar solvent and a non-polar solvent, whereas the prior art teaches use of polar solvents only. Acidic fractions prepared by using only polar solvents contain compounds that are not soluble in apolar solvents such as hexane, whereas these compounds are not present in the acidic fraction of the current invention. Accordingly, the fractions of the invention comprise a combination of compounds which differs from that disclosed in the prior art. Moreover, the inventors of the present invention have discovered that the acidic fraction of the invention unexpectedly possesses a range of highly unexpected therapeutic activities that are not suggested by the prior art.

The teachings of the present invention have been exemplified with mastic gum extracts prepared by a three-step extraction procedure, so as to obtain an acidic fraction that is soluble in both a polar solvent and a non-polar solvent, and wherein material from the mastic gum that is soluble in the polar solvent but remains insoluble in the non-polar solvent is eliminated. In further embodiments, main compounds of the isolated acidic fraction have been isolated and identified. Various combinations of some of these compounds exhibit an unexpected synergistic effect in the treatment of various impaired neurological functions (such as, for example, stroke), and in the treatment of related neurodegenerative disorders such as Alzheimer's disease.

Without wishing to be bound by any particular theory or mechanism of action, the activity of the isolated acidic fractions of mastic gum disclosed herein renders the present invention useful for various disease or conditions associated with impaired neuronal conditions, such as, for example, reformation of inter-neuronal junctions and overcoming defective inter-neuronal communication in brain and neural tissue affected by pathologies associated with inadequate synaptic formation. This pathology underlies many nervous system pathologies, including for example Alzheimer's disease. It is shown that the activity of the isolated acidic fractions of mastic gum may be used for the treatment of stroke. The invention may be further useful for promoting wound healing and rejuvenation of a large number of cells and tissues. The invention may also be useful for extending the life span of animals.

It is to be further understood that the biological activity of the fractions and compositions disclosed herein is inhibited by the presence of certain compounds that are be present in acidic fractions that have been prepared without applying the first two extraction steps as disclosed herein.

According to some embodiments, the present invention provides a composition comprising an effective amount of an isolated acidic fraction of mastic gum, and a pharmaceutically acceptable carrier; wherein the fraction is characterized in that it is soluble in at least one polar organic solvent and soluble in at least one non-polar organic solvent, and wherein said fraction is substantially devoid of compounds which are soluble in said polar organic solvent but insoluble in said non-polar organic solvent.

In some embodiments, the composition is obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treating the solution obtained in step (g) with a basic solution so as to obtain a basic fraction; and
(i) acidifying the basic fraction obtained in step (h) with an acid solution;

In some embodiments, steps (d) to (f) may precede steps (a) to (c).

In some embodiments, the treatment with a basic solution (basifying) in step (h) comprises extracting the solution obtained in step (g) with one or more suitable basic aqueous solutions; or contacting the solution obtained in step (g) with a basic ion exchange resin.

In some embodiments, step (h) comprises contacting the solution obtained in step (g) with a basic ion exchange resin, and thereafter removing the basic ion exchange resin by filtration. In these embodiments, step (i) comprises treating the basic ion exchange resin with an acidic solution.

In some embodiments, the process further comprises the steps of
(j) extracting the acidified fraction obtained in step (i) with an organic solvent;
k) optionally contacting the organic fraction obtained in step (j) with a drying agent so as to remove remaining water;
(l) removing organic solvent and/or excess acid from the fraction obtained in any of steps (i), (j) or (k); and
(m) dissolving the isolated fraction obtained in step (l) in a carrier.

In some embodiments, steps (a) to (c) are carried out prior to steps (d) to (f); or steps (d) to (f) are carried out prior to steps (a) to (c). In some embodiments, (a) to (c) and/or steps (d) to (f) are repeated for a multiplicity of cycles.

In some embodiments, any of steps (c), (f) and (l) comprise removing the solvent by a means selected from the group consisting of rotary evaporation, application of high vacuum and a combination thereof.

In some embodiments, step (h) comprises extracting the solution obtained in step (g) with a basic aqueous solution, and collecting the organic fraction thus obtained. In some embodiments, the process further comprises combining the organic fraction obtained from step (h) with a fraction obtained in any of steps (i), (j) or (k).

In some embodiments, the organic fraction obtained in step (h) is combined with a fraction obtained in any of steps (i), (j) or (k) in an amount in the range from about 0.1% to about 50% of the organic fraction obtained from step (h). In some embodiments, the amount is in the range from 0.5 to 50%; or 2 to 25%; or 0.1 to 10%.

Polar organic solvents suitable for use in the invention may be selected from an alcohol, an ether, an ester, an amide, an aldehyde, a ketone, a nitrile, and combinations thereof.

Specific examples of suitable polar organic solvents include methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

In some embodiments, the polar organic solvent is selected from methanol and ethanol or a combination thereof.

In some embodiments, the polar solvent is ethanol.

Non-polar organic solvents suitable for use in the invention may be selected from acyclic or cyclic, saturated or unsaturated aliphatic hydrocarbons and aromatic hydrocarbons, each of which is optionally substituted by one or more halogens, and combinations thereof. In some embodiments, the non-polar organic solvent is selected from C5-C10 alkanes, C5-C10 cycloalkanes, C6-C14 aromatic hydrocarbons and C7-C14 perfluoroalkanes, and combinations thereof.

In some embodiments, the non-polar organic solvent is selected from pentanes, hexanes, heptanes, octanes, nonanes, decanes, cyclopentane, cyclohexane, cycloheptane, benzene, toluene, xylene, and isomers and mixtures thereof.

In some embodiments, the C5-C10 alkane is selected from the group consisting of pentane, hexane, heptane, octane, nonane, decane, cyclohexane, and isomers and mixtures thereof.

In some embodiments, the non-polar organic solvent is hexane.

In some embodiments, the organic solvent in step (g) and in step (j) is independently selected from the group consisting of dialkyl ethers, alkyl-aryl ethers, diaryl ethers, esters, ketones, halogenated hydrocarbons, C5-C14 aromatic hydrocarbons, C5-C14 perfluoroalkanes.

In some embodiments, the suitable organic solvent in step (g) and in step (i) is the same or different.

In some embodiments, the organic solvent comprises a dialkyl ether.

In some embodiments, the organic solvent is diethyl ether.

In some embodiments, the polar organic solvent comprises ethanol, the non-polar organic solvent comprises hexane and the organic solvent comprises diethyl ether.

In some embodiments, step (h) comprises basifying with a basic aqueous solution. In some embodiments, the basic aqueous solution is prepared by dissolving an inorganic base in water.

In some embodiments, the inorganic base is selected from the group consisting of sodium carbonate, sodium hydroxide, potassium carbonate potassium hydroxide, ammonium hydroxide, sodium bicarbonate, sodium phosphate, lithium hydroxide, lithium carbonate, and potassium phosphate.

In some embodiments, the inorganic base is sodium carbonate. In some embodiments, the concentration of the sodium carbonate in water is in the range from 2 to 20% w/w. In some embodiments, the concentration of sodium carbonate is in the range from 3 to 15% w/w. In some embodiments, the concentration of sodium carbonate is about 5% w/w.

In some embodiments, the inorganic base is sodium hydroxide.

In some embodiments, the basic aqueous solution is prepared by dissolving a water-soluble organic base in water.

In some embodiments, the first inorganic base is about 5% w/w aqueous sodium carbonate, followed by about 4% w/w aqueous sodium hydroxide.

In some embodiments, the basifying in step (h) comprises contacting the solution obtained in step (g) with a basic ion exchange resin. In some embodiments, the basic ion exchange resin comprises styrene divinylbenzene, polyacrylic or formophenolic copolymers.

In some embodiments, basifying the solution is done to a pH of above about 7.

In some embodiments, basifying the solution is done to a pH range of 8-10.

In some embodiments, basifying the solution is done to a pH range of 10-13.

In some embodiments, basifying the solution is done to a pH of >13.

In some embodiments, the acidic solution in step (i) comprises an acidic aqueous solution or an acidic non-aqueous solution.

In some embodiments, the acidic aqueous solution in step (i) is prepared by dissolving an inorganic acid in water or by diluting a concentrated mineral acid solution.

In some embodiments, the acidic aqueous solution is a solution of hydrochloric acid or phosphoric acid.

In some embodiments, the acidic aqueous solution is a solution of hydrochloric acid.

In some embodiments, the acidic aqueous solution in step (i) is prepared by dissolving an organic acid in water or by diluting a concentrated mineral acid solution.

In some embodiments, acidifying is done to a pH of below about 7. In some embodiments, acidifying is done to a pH of below about 6. In some embodiments, acidifying is done to a pH of below about 5. In some embodiments, acidifying is done to a pH of below about 4. In some embodiments, acidifying is done to a pH of below about 3.

In some embodiments, acidification is done to a pH in the range of 1-3.

In some embodiments, the acidic non-aqueous solution in step (i) is prepared by dissolving an organic acid in a non-aqueous organic solvent selected from an alcohol, an ester, an ether, an amide or mixtures thereof. In some embodiments, the non-aqueous solvent is methanol or ethanol or a mixture thereof.

In some embodiments, the organic acid is selected from the group consisting of formic acid, acetic acid, propionic acid, citric acid, tartaric acid, methane sulphonic acid, and para-toluenesulphonic acid.

In some embodiments, the drying agent used in step (k) is selected from the group of sodium sulfate, magnesium sulfate, calcium sulfate, calcium chloride, magnesium chloride, potassium sulfate.

In some embodiments, the composition is substantially devoid of terpene compounds which are soluble in said polar organic solvent and insoluble in said non-polar organic solvent.

In some embodiments, the composition comprises from about 0.01 to about 25% (w/w) of the isolated acidic fraction of mastic gum, based on the total weight of the composition. In some embodiments, the composition comprises from about 0.01 to about 12% (w/w) of the isolated acidic fraction of mastic gum, based on the total weight of the composition.

In some embodiments, the isolated acidic fraction comprises at least one of: masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; oleanonic acid; moronic acid; and 3-oxo-lup-20(29)-en-28-oic acid. Each possibility is a separate embodiment of the invention.

In some embodiments, the isolated acidic fraction further comprises at least one of: oleanolic acid; ursonic acid; and ursolic acid. Each possibility is a separate embodiment of the invention.

In some embodiments, the isolated acidic fraction is substantially devoid of masticadienoic acid.

In some embodiments, the isolated acidic fraction may be substantially devoid of essential oils.

In some embodiments, the isolated acidic fraction comprises at least one terpenoic acid.

In some embodiments, the isolated acidic fraction comprises at least one triterpenoic acid.

In some embodiments, the at least one terpenoic acid comprises at least one triterpenoic acid. In some embodiments, the at least one triterpenoic acid is selected from the group consisting of masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; oleanonic acid; moronic acid; 3-oxo-lup-20(29)-en-28-oic acid and a combination thereof. Each possibility is a separate embodiment of the invention.

In some embodiments, the at least one terpenoic acid is in monomeric form. In some embodiments, the at least one terpenoic acid is in an oligomeric form. In some embodiments, the oligomeric form is selected from the group consisting of a dimer, a trimer, and a combination thereof. Each possibility is a separate embodiment of the invention.

In some embodiments, the oligomeric form is a dimer.
In some embodiments, the oligomeric form is a trimer.
In some embodiments, the at least one triterpenoic acid is in monomeric form. In some embodiments, the at least one triterpenoic acid is in an oligomeric form. In some embodiments, the oligomeric form is selected from the group consisting of a dimer, a trimer, and a combination thereof. Each possibility is a separate embodiment of the invention.

In some embodiments, the oligomeric form is a dimer.
In some embodiments, the oligomeric form is a trimer.
In some embodiments, the isolated acidic fraction comprises a combination of monomeric and dimeric triterpenoic acids. In some embodiments, the isolated acidic fraction comprises a combination of monomeric, dimeric and trimeric triterpenoic acids.

In some embodiments, the composition comprises at least one of: masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; oleanonic acid; moronic acid; and 3-oxo-lup-20(29)-en-28-oic acid. Each possibility is a separate embodiment of the invention.

In some embodiments, the composition further comprises at least one of: oleanolic acid; ursonic acid; and ursolic acid. Each possibility is a separate embodiment of the invention.

In some embodiments, the composition comprises at least one terpenoic acid. Embodiments of terpenoic acids are as hereinbefore described.

In some embodiments, the composition comprises at least one triterpenoic acid. Embodiments of triterpenoic acids are as hereinbefore described.

In some embodiments, the composition is substantially devoid of masticadienoic acid.

In some embodiments, the mastic gum is derived from a plant classified in the family Anacardiaceae. Suitable plants include those classified in a genus selected from the group consisting of *Pistacia, Pinus, Picea, Juniperus, Alsies, Larix, Antirrhinum, Boswellia, Citrus* and *Gynura*.

In some embodiments, suitable plants are selected from the genus *Pistacia*.

In some embodiments, the species of *Pistacia* is selected from the group consisting of *P. lentiscus, P. atlantica, P. palestina, P. saportae, P. terebinthus, P. vera* and *P. integerrima*.

In some embodiments, the species of *Pistacia* is *Pistacia lentiscus* L.

In some embodiments, the isolated acidic fraction is derived from a plant material selected from the group consisting of resin, leaves, twigs, roots, flowers, seeds, buds, bark, nuts and roots.

In some embodiments, the isolated acidic fraction of mastic gum is obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treatment of the solution obtained in step (g) with a basic solution so as to obtain a basic fraction;
(i) acidifying the basic fraction obtained in step (i) with an acid solution;
(j) extracting the acidified fraction obtained in step (i with an organic solvent;
(k) optionally contacting the organic fraction obtained in step (k) with a drying agent so as to remove remaining water;
(l) removing organic solvent and/or excess acid from the fraction obtained in any of steps (i), (j) or (k); and
(m) dissolving the isolated fraction obtained in step (l) in a carrier.

In additional embodiments, the invention provides a pharmaceutical composition comprising at least one triterpenoic acid; and a pharmaceutically acceptable carrier. In some embodiments, the at least one triterpenoic acid is selected from the group consisting of masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; Masticadienoic acid, oleanonic acid; moronic acid; 3-oxo-lup-20(29)-en-28-oic acid and a combination thereof. Each possibility is a separate embodiment of the invention.

According to some embodiments, the current invention provides a pharmaceutical composition consisting essentially of isomasticadienoic acid and masticadienoic acid as the pharmaceutically active ingredients; and a pharmaceutically acceptable carrier. The combined presence of both compounds results in an enhanced/synergistic effect with respect to the composition's efficacy in the treatment of impaired neurological function (and hence treatment of neurodegenerative disorders/conditions) when compared with the efficacy of the individual compounds.

Either one of isomasticdienoic acid and masticadienoic acid may be isolated from a natural source such as mastic gum, or may be the product of a chemical synthesis.

In some embodiments, the ratio between the isomasticdienoic acid and masticadienoic acid is about 1:1 w/w.

According to some embodiments, the current invention provides a pharmaceutical composition consisting essentially of oleanonic acid, isomasticadienoic acid and masticadienoic acid as the sole pharmaceutically active ingredients; and a pharmaceutically acceptable carrier. The combined presence of all three compounds results in a clear synergistic effect with respect to composition's efficacy in the treatment of impaired neurological function and treatment of neurodegenerative disorders when compared with the efficacy of the individual compounds or a mixture of only two of these three compounds.

Any one of oleanonic acid, isomasticadienoic acid and masticadienoic acid may be either isolated from a natural source, such as mastic gum, or may be the product of a chemical synthesis.

In some embodiments, the ratio between the isomasticdienoic acid and masticadienoic acid and oleanonic acid is about 1:1:1 w/w/w.

In some embodiments, the at least one triterpenoic acid is a monomer. In some embodiments, the composition comprises monomers of oleanonic acid and moronic acid. In some embodiments, the monomers of oleanonic acid and moronic acid are the products of chemical synthesis reactions.

In some embodiments, the at least one triterpenoic acid comprises an oligomeric form. In some embodiments, the oligomeric form is selected from the group consisting of a dimer, a trimer, and a combination thereof. Each possibility is a separate embodiment of the invention. In some embodiments, the oligomeric form is a dimer.

In some embodiments, the at least one triterpenoic acid is the product of a chemical synthesis.

In some embodiments, the at least one triterpenoic acid comprising an oligomeric form is the product of a chemical synthesis. In some embodiments, the at least on triterpenoic acid is a dimeric form and is the product of a chemical synthesis.

In some embodiments, the at least one triterpenoic acid is derived from a natural source, in particular a plant source.

In some embodiments, the composition comprises a combination of different triterpenoic acids, wherein at least one triterpenoic acid is the product of a chemical synthesis and at least one other triterpenoic acid is derived from a plant source.

Natural sources include plants classified in the family Anacardiaceae. Suitable plants include those classified in a genus selected from the group consisting of *Pistacia, Pinus, Picea, Juniperus, Alsies, Larix, Antirrhinum, Boswellia, Citrus* and *Gynura*.

In some embodiments, suitable plants are selected from the genus *Pistacia*.

In some embodiments, the species of *Pistacia* is selected from the group consisting of *P. lentiscus, P. atlantica, P. palestina, P. saportae, P. terebinthus, P. vera* and *P. integerrima*.

In some embodiments, the species of *Pistacia* is *Pistacia lentiscus* L.

In some embodiments, the natural source is a plant material selected from the group consisting of resin, leaves, twigs, roots, flowers, seeds, buds, bark, nuts and roots.

In some embodiments, the natural source is a plant classified in a genus selected from the group consisting of *Ocimum, Laurus* and *Lavendula*.

In some embodiments, the pharmaceutically acceptable carrier comprises a hydrophobic carrier. In some embodiments, the hydrophobic carrier comprises at least one oil. In some embodiments, the oil is selected from the group consisting of a mineral oil, a vegetable oil and combinations thereof. In some embodiments, the vegetable oil is selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the mineral oil is light mineral oil. In some embodiments, the hydrophobic carrier comprises at least one wax. In some embodiments, the hydrophobic carrier comprises a combination of at least one oil and at least one wax.

In various embodiments, a composition according to the invention is in a form suitable for administration by a route selected from the group consisting of parenteral, transdermal, oral and topical.

In various embodiments, a composition according to the invention is in a form suitable for topical administration.

In various embodiments, a composition according to the invention is in a form suitable for oral administration.

In various embodiments, a composition according to the invention is in a form suitable for parenteral administration.

In some embodiments, the composition is in a form suitable for administration by injection. In various embodiments, the composition is a parenteral formulation for administration by a route selected from the group consisting of subcutaneous, intravenous, intramuscular, intradermal, intraperitoneal, intraarterial, intracerebral, intracerebroventricular, intraosseus and intrathecal.

In some embodiments, the composition is a parenteral formulation for administration by subcutaneous route.

In various embodiments, the composition is a formulated for administration by a route selected from the group consisting of dermal, vaginal, rectal, inhalation, intranasal, ocular, auricular and buccal.

In some embodiments, the composition is in a form suitable for cosmetic or dermatologic administration.

In some embodiments, the pharmaceutical composition is in a form selected from the group consisting of a capsule, a tablet, a liposome, a suppository, a suspension, an ointment, a cream, a lotion, a solution, an emulsion, a film, a cement, a powder, a glue, an aerosol and a spray. In some embodiments, the capsule is selected from the group consisting of a hard gelatin capsule and a soft gelatin capsule. In some embodiments, the emulsion is a nanoemulsion or a microemulsion.

In some embodiments, the formulation comprises at least one of an inclusion complex, a nanoemulsion, a microemulsion, a powder, a lipid raft, a lipid microparticle, a dendrimer and a liposome. In some embodiments, the inclusion complex comprises at least one cyclodextrin. In some embodiments, the at least one cyclodextrin comprises hydroxypropyl-β-cyclodextrin. In some embodiments, the nanoemulsion comprises droplets having average particle size of less than 800 nm. In some embodiments, the droplets have average particle size of less than 500 nm. In some embodiments, the droplets have average particle size of less than 200 nm. In some embodiments, the powder is a spray dried powder. In some embodiments, the liposome comprises a multilamellar vesicle. In some embodiments, the microemulsion comprises a non-ionic surfactant. In some embodiments, the non-ionic surfactant is selected from the group consisting of a polyoxyl castor oil, a polyoxyethylene sorbitan fatty acid ester (polysorbates), a poloxamer, a vitamin E derivative, a polyoxyethylene alkyl ether, a polyoxyethylene sterate, or saturated polyglycolyzed glyceride or combinations thereof.

In some embodiments, the composition is disposed on the article of manufacture in the form of a coating. In some embodiments, the article of manufacture comprises a vessel, wherein the composition is disposed within the vessel. In some embodiments, the article of manufacture is selected from the group consisting of a fabric article, a diaper, a wound dressing, a medical device, a needle or plurality of needles, a microneedle or plurality of microneedles, an injection device and a spray dispenser. In some embodiments, the article of manufacture comprises a plurality of microneedles. In some embodiments, the medical device is selected from the group consisting of a prosthetic, an artificial organ or component thereof, a valve, a catheter, a tube, a stent, an artificial membrane, a pacemaker, a sensor, an endoscope, an imaging device, a pump, a wire and an implant. In some embodiments, the implant is selected from the group consisting of a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the composition is suitable for administration by a means selected from the group consisting of electroporation, sonication, radio frequency, pressurized spray and combinations thereof.

In some embodiments, the composition is used for treating impaired neurological function. In some embodiments, the impaired neurological function comprises a decrease in a function selected from the group consisting of cognitive function, sensory function, motor function and combinations thereof. In some embodiments, the impaired neurological function is associated with a condition or disease. In some embodiments, the condition or disease is selected from the group consisting of Alzheimer's disease, amyotrophic lateral sclerosis (ALS), multiple sclerosis, Parkinson's disease, vascular dementia and senile dementia. In some embodiments, the condition is trauma or stroke.

In some embodiments, the condition or disease is a psychiatric disorder, such as schizophrenia, bipolar disorder or depression.

In some embodiments, the condition or disease is selected from obesity, anorexia, cachexia, an infection and an immunological disorder.

In some embodiments, the impaired neurological function is due to exposure to a drug, such as an anesthetic.

In some embodiments, the condition or disease is selected from the group consisting of vascular dementia, senile dementia, Alzheimer's disease, amyotrophic lateral sclerosis (ALS), multiple sclerosis, Parkinson's disease and stroke.

In some embodiments, the condition is stroke.
In some embodiments, the condition is trauma.
In some embodiments, the condition or disease is selected from the group consisting of vascular dementia, senile dementia, Alzheimer's disease, amyotrophic lateral sclerosis (ALS) and multiple sclerosis.

In some embodiments, the condition or disease is selected from the group consisting of vascular dementia, senile dementia, Alzheimer's disease and amyotrophic lateral sclerosis (ALS).

In some embodiments, the condition or disease is selected from the group consisting of vascular dementia, senile dementia and Alzheimer's disease.

In some embodiments, the disease is Alzheimer's disease.
In some embodiments, the disease is amyotrophic lateral sclerosis (ALS).

In some embodiments, the composition is for treating a skin wounds, including for example, a venous leg ulcer, a pressure ulcer, a diabetic foot ulcer, a burn, an amputation wound, a decubitus ulcer (bed sore), a split-skin donor graft, a skin graft donor site, a medical device implantation site, a bite wound, a frostbite wound, a puncture wound, a shrapnel wound, a dermabrasion, a contusion, an infection, a wound and a surgical wound.

In some embodiments, the composition is for inducing or promoting tissue repair. As used herein, tissue repair encompasses induction and promotion of tissue regeneration, including of neural tissues.

In some embodiments, the composition is for inducing or promoting tissue repair following an injury or insult. In some embodiments, the injury or insult is selected from the group consisting of a myocardial infarction, a pulmonary embolism, a cerebral infarction, peripheral artery occlusive disease, a hernia, a splenic infarction, a venous ulcer, an axotomy, a retinal detachment, an infection and a surgical procedure.

In some embodiments, the composition is used for inducing or promoting life span extension in animals. In some embodiments, the animals are selected from the group of humans, non-human mammals, birds and fish.

Other objects, features and advantages of the present invention will become clear from the following description and drawings.

BRIEF DESCRIPTION OF THE DRAWINGS

FIG. 3B is the peak list for FIG. 3A.

DETAILED DESCRIPTION OF THE INVENTION

Figure 1:
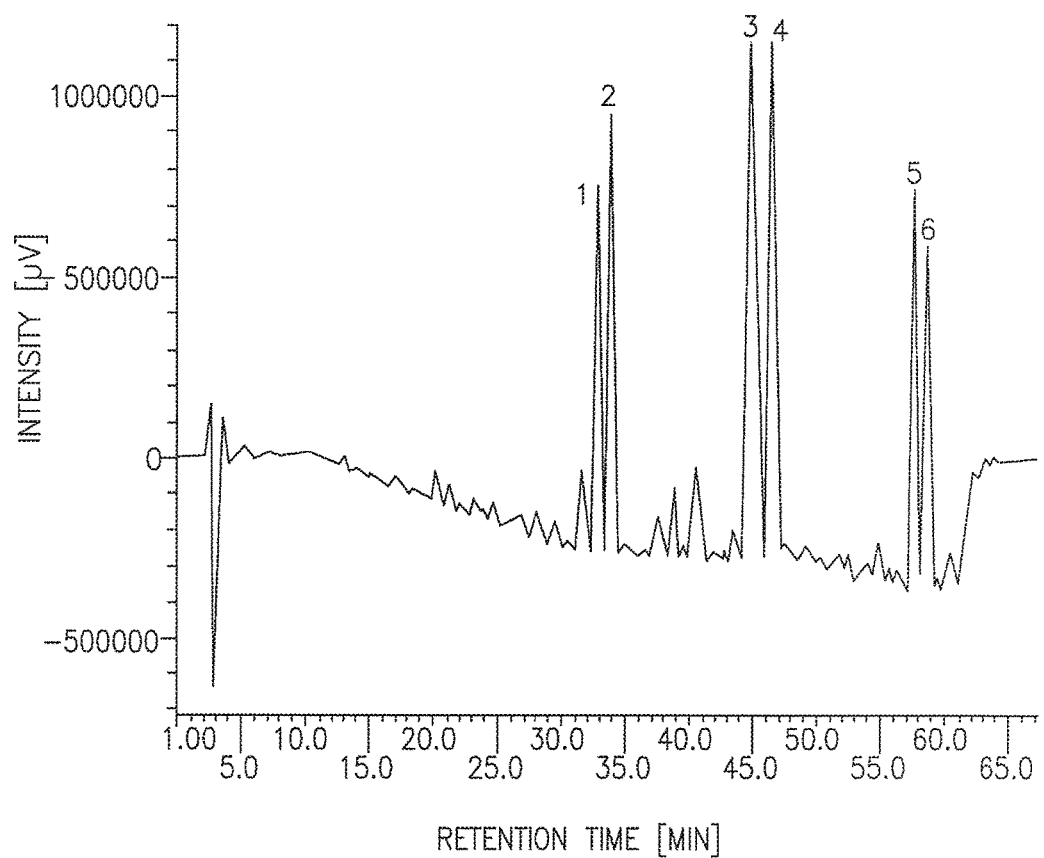
FIG. 1 shows a reversed phase HPLC chromatogram of an isolated acidic fraction according to the invention. The chromatogram was obtained using a UV-VIS detector at wavelength 205 nm detection.
Figure 2A:
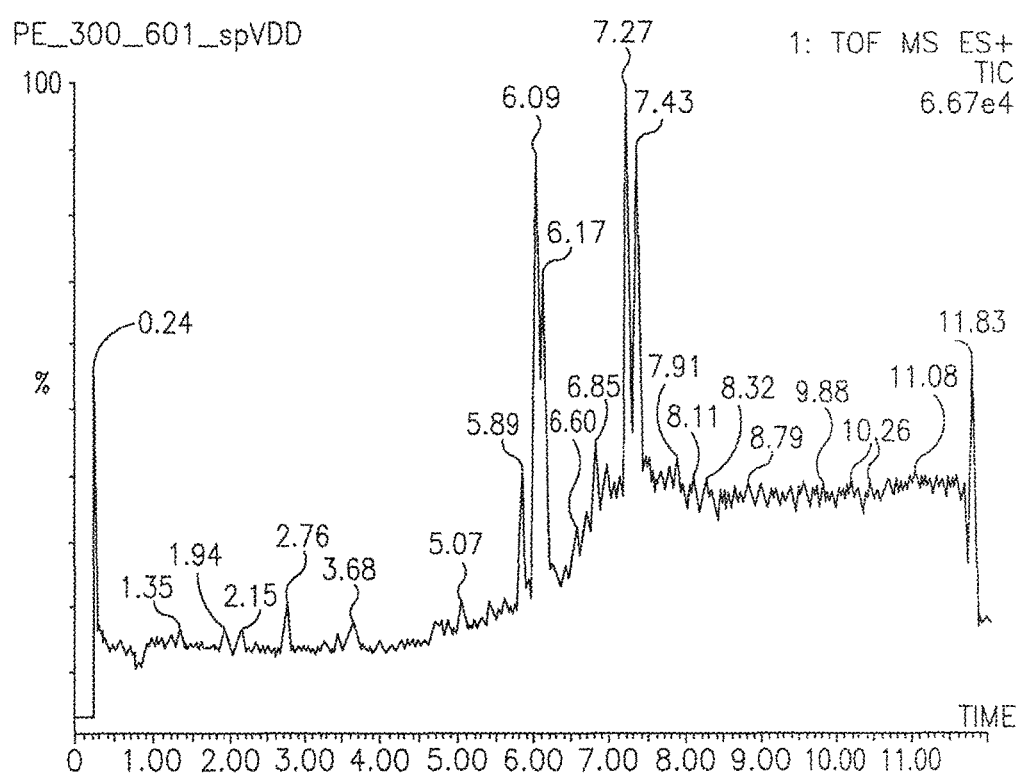
FIG. 2A shows an LC-MS chromatogram of an isolated acidic fraction according to the invention, indicative of a mixture of triterpenoic acid dimers
Figure 2B:
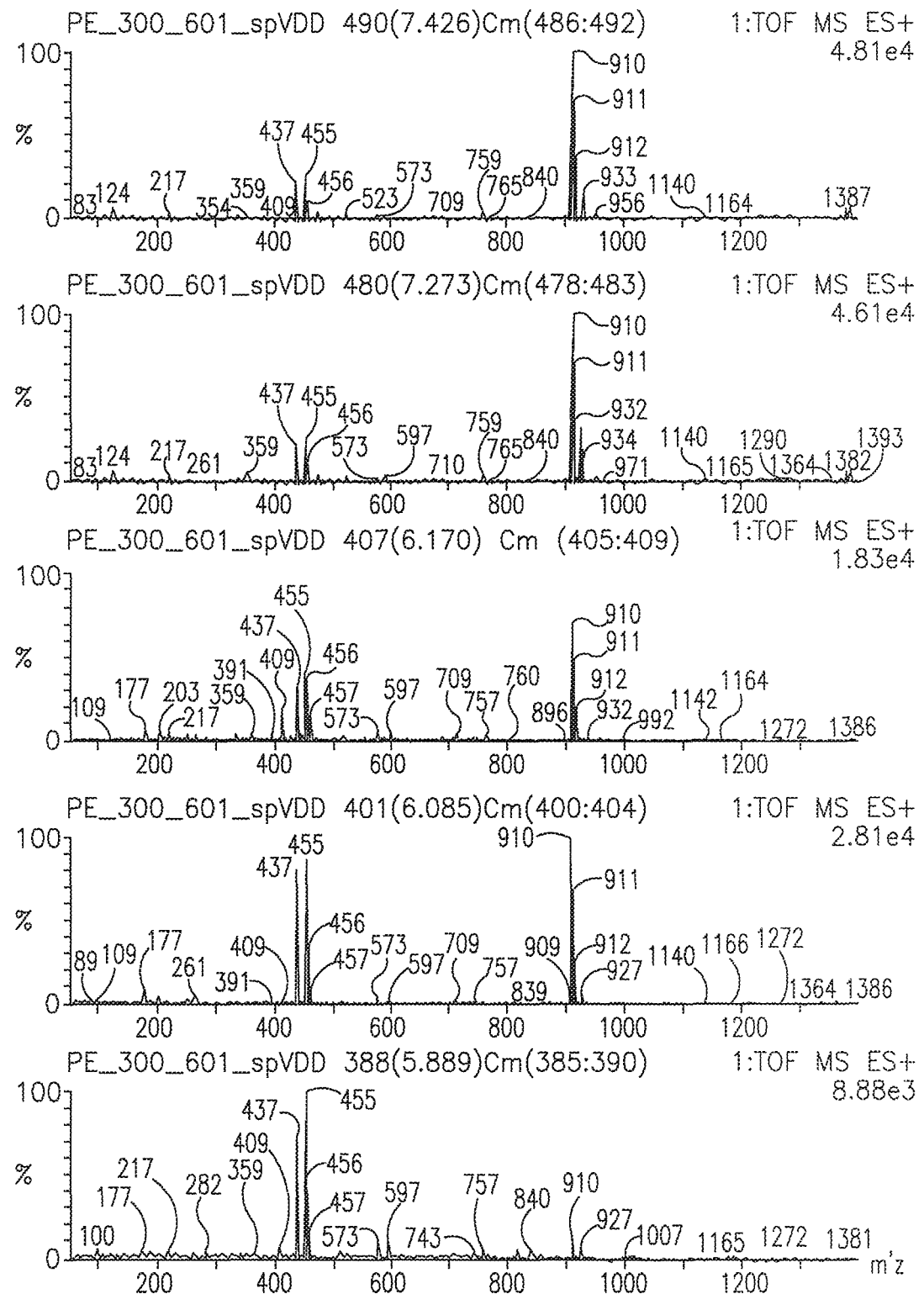
FIG. 2B shows the mass spectra of the main peaks of the chromatogram of FIG. 2A.
Figure 2C:
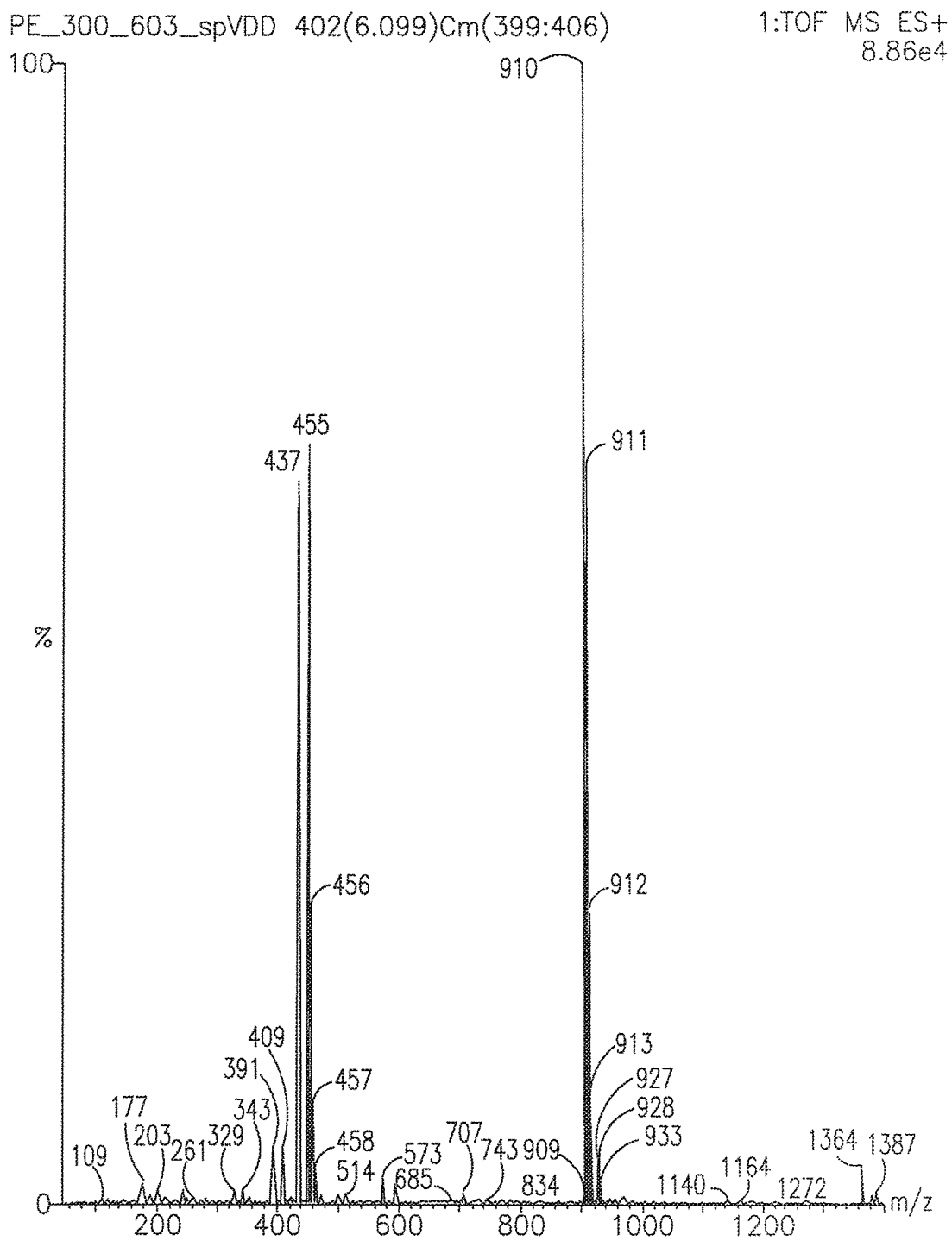
FIG. 2C shows an enlarged mass spectrum of the peak at retention time 6.09 min, shown in FIG. 2A.
Figure 2D:
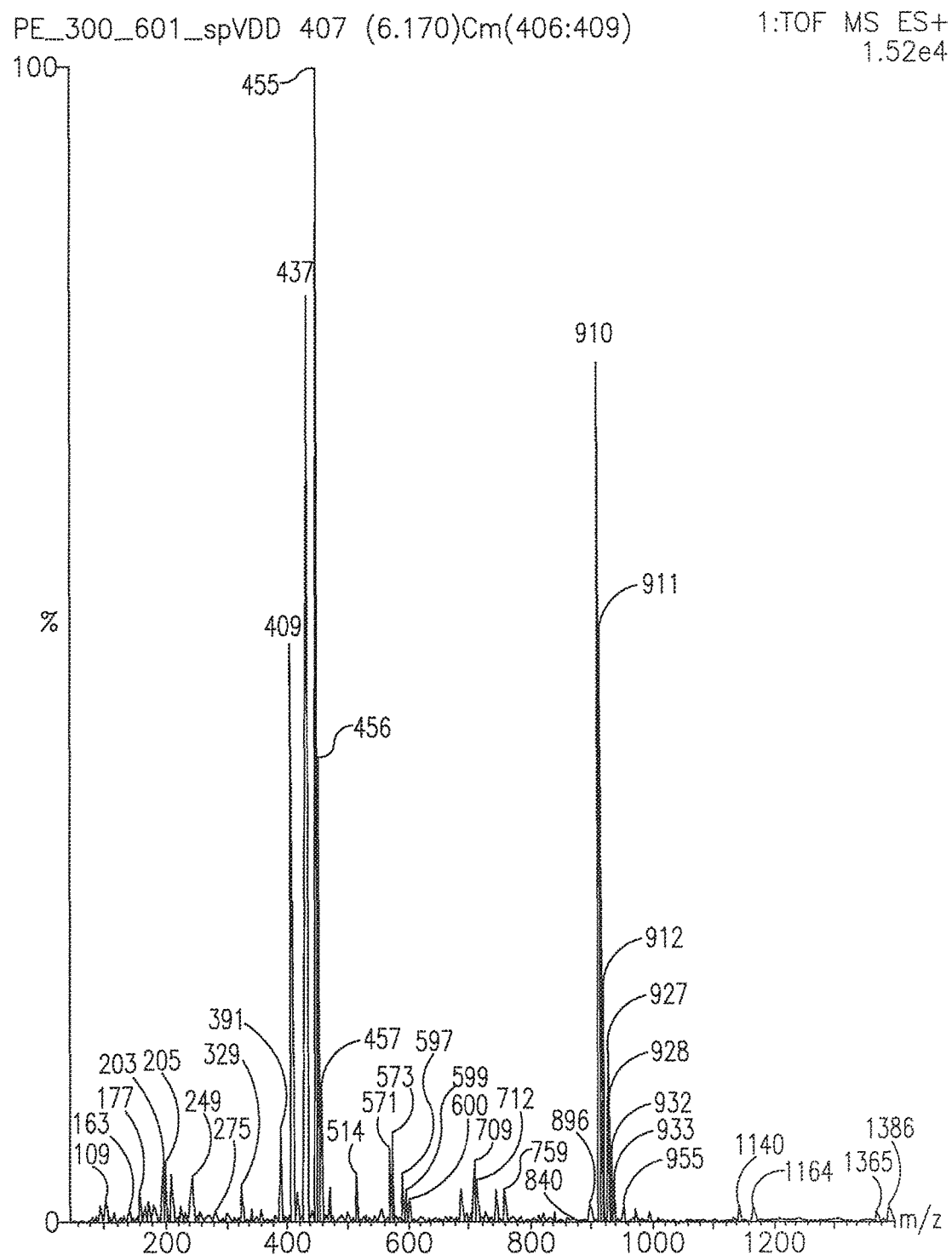
FIG. 2D shows an enlarged mass spectrum of the peak at retention time 6.17 min, shown in FIG. 2A.
Figure 3A:
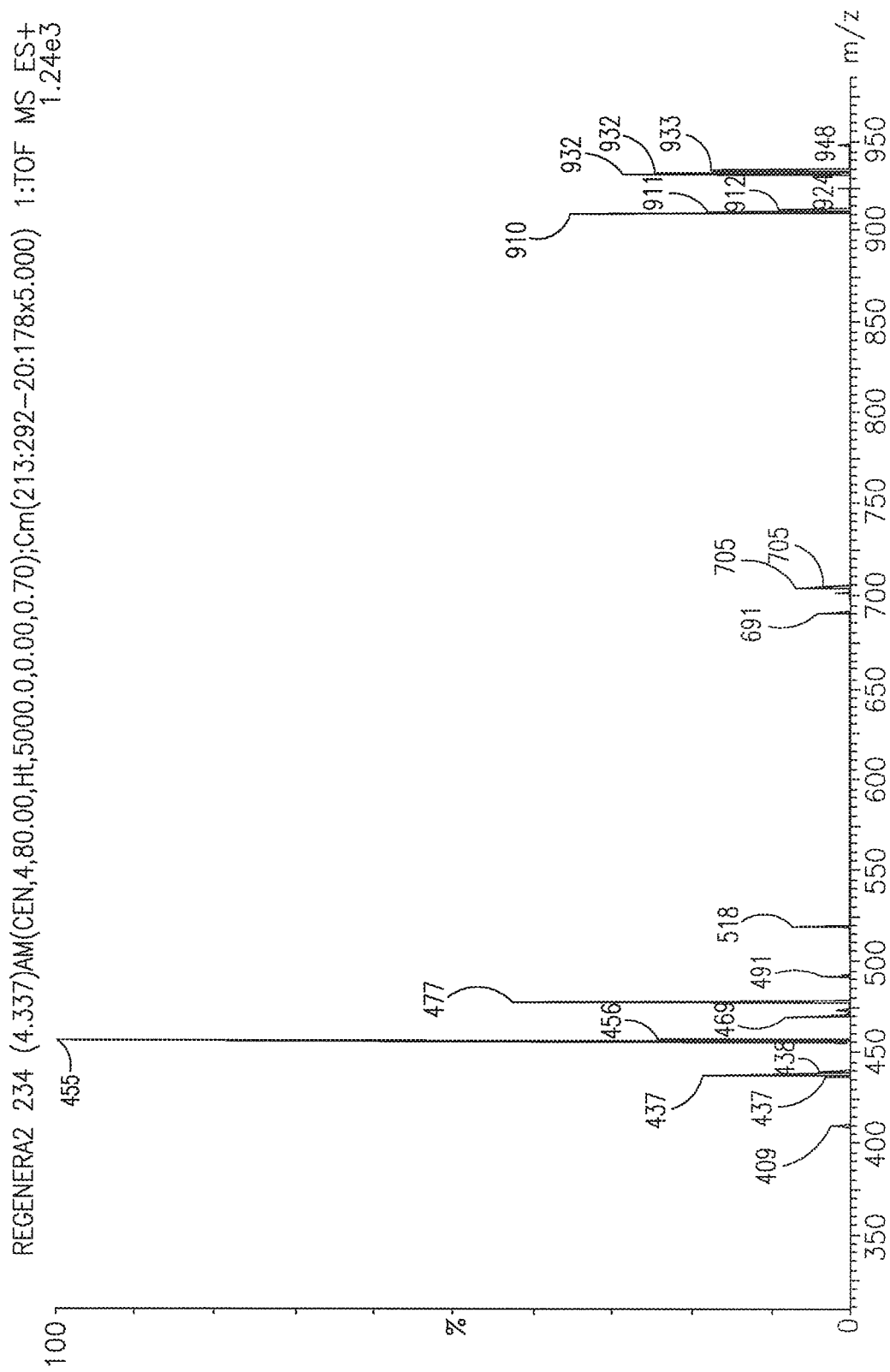
FIG. 3A shows a TOF mass spectrum of an isolated acidic fraction of mastic gum, indicative of a mixture of monomeric and dimeric triterpenic acids.

The inventors of the present invention have surprisingly found that isolated acidic fractions of mastic gum show high activity in ameliorating or reversing impaired neurological function, stroke recovery, healing of skin wounds, promoting tissue repair, and in promoting life span extension in animals.

It is herein disclosed for the first time that owing to its various activities in stimulating and inducing cell regeneration, the isolated acidic fraction of mastic gum, as well as combinations of compounds isolated therefrom, as described herein may be employed as an active ingredient in a pharmaceutical composition for a number of therapeutic indications.

Advantageously, the compositions of the invention may be used in methods of treating impaired neurological function and skin conditions. Upon contact with cells of both human and non-human subjects, the composition induces cell differentiation in a wide array of tissues, cell compartments and cell lineages, including skin, endothelium, mucous membranes, bones, tendons and cartilage. In addition, the cell differentiation activity of the pharmaceutical composition may be exploited for promoting in vivo incorporation of medical devices, implants and organ transplants. Furthermore, the pharmaceutical composition may be used to promote life span extension in animals.

Definitions

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. Chia (cultivated on the Greek island of Chios), are known for their high yield of mastic. Other varieties include *P. lentiscus* L. var. *emarginata* Engl., and *P. lentiscus* L. var. *latifolia* Coss. Additional species of *Pistacia* include for example, *P. atlantica, P. palestina, P. saportae, P. terebinthus, P. vera* and *P. integerrima*.

As used herein, the term "isolated acidic fraction of mastic gum" refers to a fraction obtained following extraction of gum mastic with at least one polar and at least one non-polar organic solvent, followed by an acid-base extraction of a solution of the thus obtained material and isolation of the resulting acidic fraction. The isolated acidic fraction of the invention is soluble both in polar and non-polar organic solvents.

As used herein the term "plurality" refers to more than one, preferably more than two. As used herein the term "synergistic" means more than additive.

As used herein, the term "acid-base extraction" refers to a procedure in which an organic solvent solution containing organic acidic and organic non-acidic components is treated/extracted with one or more basic aqueous solution(s). As a result of this, the organic acidic components are deprotonated and thus converted into their corresponding ionic salt forms and as a result will dissolve in the said basic aqueous solution. The non-acidic organic components will stay behind in the original organic solution. Subsequently, the basic aqueous solution containing the salt forms of the acidic components is acidified, resulting in the reformation of the protonated acid forms of the organic acidic components. These protonated acid forms (acidic fraction) can be removed from the acidified aqueous solution in several ways depending on the properties of the acidic compounds. One option for removing the acidic fraction from the acidified solution is by extraction into a suitable organic solvent. Example 1 is a non-limiting example of an acid-base extraction as described above.

Depending on the solubility of the acidic compounds in the acidified aqueous solution, the acidic fraction may be isolated via filtration of the acidified aqueous solution.

Instead of using a basic aqueous solution for the acid-base extraction, basic forms of ion-exchange resins can be used as well. In these cases, the acidic organic components (acidic fraction) are captured in their deprotonated anionic form by the resin. The resin is subsequently removed from the initial solution, leaving non-acidic components behind. The acidic components (acidic fraction) are subsequently released from the resin by treatment of the resin with a suitable acidic solution.

The use of ion-exchange resins for acid-base extractions is especially suitable for process scale up and can be used for the development of (semi)continuous extraction processes.

Examples of the above acid-base extractions and other variations can be found in many textbooks and other publications, and are considered common knowledge to those skilled in the art. An example of a useful textbook is "Vogel's Textbook of Practical Organic Chemistry", $5^{th}$ Edition, 1989, (p. 162-163).

As used herein, the term "degree of purity" refers to the content of a specified chemical compound in a preparation, expressed as a percentage on a weight per weight basis of the specified chemical compound relative to other chemical compounds in the preparation.

As used herein, "terpene compounds" refers to isoprene-containing hydrocarbons, having isoprene units ($CH_2$=C($CH_3$)—CH=$CH_2$) in a head-to-tail orientation. Terpene hydrocarbons in general, have the molecular formula ($C_5H_8$)$_n$, and include hemiterpenes, (C5), monoterpenes (C10), sesquiterpenes (C15), diterpenes (C20), triterpenes (C30), and tetraterpenes (C40) which respectively have 1, 2, 3, 4, 6 and 8 isoprene units. Terpenes may be further classified as acyclic or cyclic.

As used herein, "terpenoids" and "terpenoid compounds" interchangeably refer to terpene-related compounds which contain oxygen in addition to isoprene units, and thus include alcohols, aldehydes and ketones. Terpenoids are subdivided according to the number of carbon atoms in a manner similar to terpene and thus include hemiterpenoids, (C5), monoterpenoids (C10), sesquiterpenoids (C15), diterpenoids (C20), triterpenoids (C30), and tetraterpenoids (C40) which respectively have 1, 2, 3, 4, 6 and 8 isoprene units. The skeleton of terpenoids may differ from strict additivity of isoprene units by the loss or shift of a fragment, generally a methyl group. Examples of monoterpenoids include camphor, eugenol and borneol. Examples of diterpenoids include phytol and taxol. Examples of triterpenoids include squalene and lanosterol.

As used herein, "terpenoic acids" refer to terpenoid compounds containing at least one carboxylic acid group. The terpenoic acids may additionally contain one or more other oxygen-containing functional groups comprising hydroxyl, keto, aldehyde, ether (cyclic and non-cyclic) and ester (cyclic and non-cyclic) groups.

As used herein, "triterpenoic acids" refer to triterpenoid compounds containing at least one carboxylic acid group. The triterpenoic acids may additionally contain one or more other oxygen-containing functional groups comprising hydroxyl, keto, aldehyde, ether (cyclic and non-cyclic) and ester (cyclic and non-cyclic) groups.

As used herein, "an oligomeric form of a terpenoic acid" refers to an oligomeric terpenoid acid in which the monomeric units are either of the same terpenoic acid or of different terpenoic acids, and are joined in any possible arrangements, and are connected one to another through any possible bond or functional group, such as a C—C bond, an ester group or an ether group.

As used herein, "an oligomeric form of a triterpenoic acid" refers to an oligomeric triterpenoid acid in which the monomeric units are either of the same triterpenoic acid or of different triterpenoic acids, and are joined in any possible arrangements, and are connected one to another through any possible bond or functional group, such as a C—C bond, an ester group or an ether group.

As used herein, the terms "masticadienoic acid", "masticadienonic acid", "masticadienoic" and "masticadienonic acid" may interchangeably be used.

As used herein, the terms "isomasticadienoic acid", "isomasticadienonic acid", "isomasticadienoic" and "isomasticadienonic" may interchangeably be used.

As used herein, "substantially devoid" means that a preparation or pharmaceutical composition according to the invention that generally contains less than about 5% of the stated substance. For example, less than about 3%, less than 1%, less than 0.5%, less than 0.1%.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which a mastic fraction is dissolved or suspended.

As used herein, "cell differentiation" refers to the process in which a less specialized cell becomes a more specialized cell. Cell differentiation may be established on the basis of changes in any of a number of cellular characteristics, including but not limited to size, shape, organelle appearance, membrane potential, metabolic activity, and responsiveness to signals. A particular "grade" may be given to a cell type to describe the extent of differentiation.

As used herein, "impaired neurological function" refers to a decline or decrease in at least one of sensory, cognitive or motor function, as compared to a previous level of function or activity, and/or as compared to non-impaired individuals matched according to accepted criteria.

As used herein the term "about" in reference to a numerical value stated herein is to be understood as the stated value +/−10%.

Triterpenoic Acids and Isolated Acidic Fractions Comprising Terpenoic Acids

In some embodiments, the present invention provides compositions comprising specific combinations of terpenoic acids, such as that found in isolated acidic fractions of mastic gum. In some embodiments, the present invention provides compositions consisting of specific triterpenoic acids compounds, these compositions are shown to have an unexpected synergetic effect compared to the same individual triterpenoic acids compounds in the treatment of neurological disorders. The triterpenoic acid compounds may be from a plant source, in particular mastic gum, or may be the products of chemical synthesis reactions. In some cases, the compositions may correspond to combinations of compounds, in which some are chemically synthesized and some are derived from plant sources.

Plant species useful for obtaining the compositions of the invention include without limitation, those of the genera *Pistacia, Pinus, Picea, Juniperus, Alsies, Larix, Ocimum, Laurus* and *Lavendula*.

Useful species of *Pistacia* include without limitation, *P. lentiscus, P. atlantica, P. palestina, P. saportae, P. terebinthus, P. vera* and *P. integerrima*.

Commercial preparations of mastic are available for example, from the Chios Gum Mastic Growers Association, or from G. Baldwin & Co., U.K.

Analytical methods for determining the precise chemical composition of the obtained isolated acidic fraction of mastic gum include nuclear magnetic resonance (for example $^1$HNMR and $^{13}$CNMR), viscometry, various mass spectrometry methods (for example MALDI-TOF), HPLC, combination methods such as Liquid Chromatography-Mass spectrometry (LC-MS), UV-VIS spectrometry, IR and FT-IR spectrometry and other methods as are known in the art.

The method used for obtaining isolated acidic fractions of mastic gum can be described as follows. By way of a general description, collected plant material, for example mastic gum, is combined in a suitable vessel with a suitable solvent, usually a polar solvent. Suitable polar solvents include for example, alcohols, ethers, esters, amides, aldehydes, ketones, nitriles and combinations thereof.

Particular examples of polar organic solvents are methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

The mastic gum and the solvent are preferably combined such that the solvent is in large excess, for example 10:1 or 20:1. The mixture may be periodically or continuously agitated over a period ranging from a few minutes to a number of hours. The solvent may be decanted without any treatment, or optionally the mixture may be first subjected to low speed centrifugation, for example at 100 to 2000 rpm, as is known in the art. The insoluble material is recovered from the extract and a fresh aliquot of solvent is added to the insoluble material, such that the extraction and dissolution process is repeated for a number of cycles, in order to obtain as much as possible of the polar solvent soluble compounds. After the final dissolution step, the extracts containing polar solvent soluble material are combined and the polar solvent is evaporated (for example by using a rotary evaporation as is known in the art), so as to yield polar solvent soluble material, which may be referred to as a crude, or "first step" extract.

The first step extract material is combined with a non-polar organic solvent and extracted by shaking over a period of 1 to 2 hours. Suitable non-polar solvents include acyclic or cyclic, saturated or unsaturated aliphatic hydrocarbons and aromatic hydrocarbons, for example, C5-C10 alkanes, C5-C10 cycloalkanes, C6-C14 aromatic hydrocarbons, and combinations thereof. Each of the foregoing may be optionally substituted by one or more halogens, for example, C7-C14 perfluoroalkanes. Particular examples of non-polar organic solvents are pentanes, hexanes, heptanes, octanes, nonanes, decanes, cyclopentane, cyclohexane, cycloheptane, benzene, toluene, xylene, and isomers and mixtures thereof. Material remaining insoluble or precipitating in the presence of the non-polar solvent is removed and discarded. The non-polar solvent-soluble fraction is then obtained by evaporating the non-polar solvent (for example by rotary evaporation). This fraction may be referred to as purified or "two step" extract, corresponding to an isolated fraction of mastic gum which is characterized by the fact that it is soluble in both a polar solvent and a non-polar solvent, while materials which are soluble in the polar solvent but insoluble in the non-polar solvent, have been removed.

The second step extract material is subsequently dissolved in an organic solvent and this solution is extracted repeatedly (e.g. four times) with a basic aqueous solution. A second extraction with a different basic aqueous solution may be performed. The basic fraction thus obtained is acidified with a dilute aqueous acid solution to acidic pH. The acidified aqueous solution is extracted several times with an organic solvent. The thus obtained combined organic solvent extracts (also referred to as "three step extract") are treated with a drying agent. This isolated acidic fraction of mastic gum is then obtained by evaporating the organic solvent (for example by rotary evaporation). This fraction is referred to as the isolated acidic fraction of mastic gum. Additional intermediate steps of drying and/or solvent removal may be carried our between other steps, as is known in the art. Alternately, the second step extract material may be combined with a basic ion exchange resin e.g. Amberlyst® A26. The isolated ion-exchange resin is treated with an non-aqueous acidic solution in order to liberate the acidic fraction from the resin. The isolated acidic fraction is then obtained by evaporating the non-aqueous solvent and any excess acid.

The feature that distinguishes the isolated acidic fractions of the invention over prior art extracts of mastic gum is that certain acidic compounds have been removed in the first two steps of the procedure which would otherwise end up in the final acidic fraction. According to the teachings of the present invention, the acidic compounds removed during the first two steps of the isolation procedure have a detrimental effect on the beneficial biological activities of the isolated acidic fractions disclosed herein.

The three step extract may be dried further, for example by high vacuum treatment (for example <0.01 mbar for up to several days) to remove residual solvent and other volatile material, weighed and combined with a non-polar organic solvent or other carrier to effect its dissolution.

In some embodiments, the isolated fraction of the invention may be obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said non-polar organic solvent;
(f) optionally removing said non-polar organic solvent;
(g) dissolving the fraction obtained in step (f) in an organic solvent;
(h) treating the solution obtained in step (g) with a basic solution so as to obtain a basic fraction; and (i) acidifying the basic fraction obtained in step (h) with an acid solution.

In some embodiments, the treatment with a basic solution (basifying) in step (h) comprises extracting the solution obtained in step (g) with one or more suitable basic aqueous solution; or contacting the solution obtained in step (g) with a basic ion exchange resin. In case of a basic ion exchange resin, the resin may subsequently be treated with an acidic solution in order to release the captured acidic fraction. The isolated acidic fraction is than obtained by removal of any volatiles using, for example, application of vacuum.

In some embodiments, step (h) comprises contacting the solution obtained in step (g) with a basic ion exchange resin, and thereafter removing the basic ion exchange resin by filtration. The basic ion exchange resin may be subsequently treated with an acidic solution in order to liberate the captured acidic fraction. The isolated acidic fraction is than obtained by removal of any volatiles using e.g. application of vacuum.

In some embodiments, the process further comprises the steps of
(j) extracting the acidified fraction obtained in step (i) with an organic solvent;
k) optionally contacting the organic fraction obtained in step (j) with a drying agent so as to remove remaining water;
(l) removing organic solvent and/or excess acid from the fraction obtained in any of steps (i), (j) or (k); and
(m) dissolving the isolated fraction obtained in step (l) in a carrier.

The process may further comprise removing the solvent after any of steps (c), (f) or (l). Solvent removal may be carried out by any means known in the art, for example rotary evaporation, application of high vacuum and a combination thereof. In some embodiments, steps (a) to (c) are carried out prior to steps (d) to (f) or vice versa. In some embodiments, the polar organic solvent comprises ethanol, the non-polar organic solvent comprises hexane and the organic solvent used for the acid-base extraction comprises diethyl ether. As is readily understood by one of skill in the art, steps (a) to (c) and steps (d) to (f) may each be independently carried out for a number of cycles to optimize the extraction process and degree of purification of the product.

In some embodiments, step (h) comprises extracting the solution obtained in step (g) with a basic aqueous solution, and collecting the organic fraction obtained therefrom. In some embodiments, the process may further comprise combining the organic fraction obtained from step (h) with a fraction obtained in any of steps (i), (j) or (k).

In some embodiments, the organic fraction obtained in step (h) is combined with a fraction obtained in any of steps (i), (j) or (k) in an amount in the range from about 0.1 to 50% of the organic fraction obtained from step (h). In some embodiments, the amount is in the range from about 0.5-50%; or 2 to 25%; or 0.1 to 10%.

The isolated acidic fraction may comprise at least one terpenoic acid, such as a combination of various triterpenoic acid combinations. Triterpenoic acids include for example, masticadienolic acid; isomasticadienoic acid; isomasticadienolic acid; 3-O-acetyl masticadienolic acid; 3-O-acetyl epi-masticadienolic acid; 3-O-acetyl isomasticadienolic acid, 3-O-acetyl epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, for example, masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least three terpenoic acid compounds, selected from, masticadienolic acid; isomasticadienoic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; oleanonic acid; oleanolic acid; ursonic acid; ursolic acid; moronic acid; and 3-oxo-lup-20(29)-en-28-oic acid.

In some embodiments, the isolated acidic fraction may comprise at least two terpenoic acid compounds, selected from, masticadienolic acid, isomasticadienoic acid, and oleanonic acid.

In some embodiments, the isolated acidic fraction may be substantially devoid of particular triterpenoic acids, such as, for example, masticadienoic acid, or moronic acid. Each possibility is a separate embodiment.

In some embodiments, the isolated acidic fraction may be substantially devoid of essential oils.

Furthermore, terpenoic acid and or triterpenoic acids in the isolated acidic fraction may be in monomeric form, or in an oligomeric form, such as a dimer, a trimer, or combinations thereof.

Pharmaceutical Compositions

The composition for use in the invention comprises a therapeutically effective amount of an isolated acidic fraction of mastic gum described herein, and a pharmaceutically acceptable hydrophobic carrier.

The invention also provides a composition comprising at least one triterpenoic acid; and a pharmaceutically acceptable carrier. The triterpenoic acid may be isolated from a plant product, such as mastic gum, as hereinbefore described, or it may be the product of a chemical synthesis. Furthermore, the composition may comprise a combination of triterpenoic acids, some of which are chemically synthesized, and some of which are isolated from one or more plant products. In some embodiments, the composition may consist of at least two triterpenoic acids compounds as the pharmaceutically active ingredients, and a pharmaceutically acceptable carrier. In addition, the composition may comprise dimeric, trimeric and higher oligomeric forms of triterpenoic acids; the oligomers can be formed from both identical and different monomeric triterpenoic acids. In some embodiments, the composition may consist of at least three triterpenoic acids compounds as the pharmaceutically active ingredients, and a pharmaceutically acceptable carrier.

For preparation of a composition for therapeutic use, suitable carriers may be used, such as hydrophobic carriers including pharmaceutically acceptable oils, optionally in combination with waxes, as described herein.

An hydrophobic carrier comprises at least one oil, such as for example a mineral oil, a vegetable oil or combinations thereof.

The term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In accordance with some embodiments of the invention, the mineral oil is light mineral oil, a commercially available product which may be obtained either as a NF (National Formulary) grade product or as a USP (US Pharmacopoeia) grade product. For use in the invention, the mineral oil is preferably free of aromatics and unsaturated compounds.

Suitable vegetable oils include, but are not limited to cottonseed oil, olive oil, almond oil, canola oil, coconut oil, corn oil, grape seed oil, peanut oil, saffron oil, sesame oil, soybean oil, or combinations thereof. In some embodiments, the mineral oil is light mineral oil.

The pharmaceutically acceptable carrier may alternately or in addition comprise an oil replacement. Oil replacements include alkanes having at least 10 carbon (e.g., isohexadecane), benzoate esters, aliphatic esters, noncomodogenic esters, volatile silicone compounds (e.g., cyclomethicone), and volatile silicone substitutes. Examples of benzoate esters include $C_{12}C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

Cyclomethicone is an evaporative silicone which may be included in the carrier to assist in making the composition amenable to ejection from a spray dispenser. Furthermore, due to its evaporative property, cyclomethicone may assist in retaining and fixing the formulation on the surface to which it is sprayed e.g. a wound site.

The hydrophobic carrier may further comprise at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

The pharmaceutical composition may be formulated in any of a number of forms such as for example, a capsule (including a sofigel capsule), a tablet, a gel, a liposome, a suppository, a suspension, an ointment, a solution, an emulsion or microemulsion, a film, a cement, a powder, a glue, an aerosol, a spray and a gel.

For preparing the pharmaceutical composition, the isolated acidic fraction of mastic gum may be suitably formulated as inclusion complexes, nanoemulsions, microemulsions, powders and liposomes. In some embodiments, an inclusion complex comprises at least one cyclodextrin. In some embodiments, cyclodextrins comprise hydroxypropyl-3-cyclodextrin. In some embodiments, nanoemulsions comprise droplets having average particle size of less than 800 nm. In some embodiments, the droplets have average particle size of less than 500 nm. In some embodiments, the droplets have average particle size of less than 200 nm. In some embodiments, powders are spray dried powders. In some embodiments, liposomes comprise multilamellar vesicles. In some embodiments, a microemulsion comprises a non-ionic surfactant. Non-ionic surfactants include, without limitation, polyoxyl castor oils, polyoxyethylene sorbitan fatty acid esters (polysorbates), a poloxamer, a vitamin E derivative, polyoxyethylene alkyl ethers, polyoxyethylene sterates, saturated polyglycolyzed glycerides or combinations thereof.

Various formulations of the isolated acidic fraction of mastic gum and preparation thereof are disclosed herein in Examples 7-11. The pharmaceutical compositions of the invention may be administered by any means that achieve their intended purpose. For example, administration may be by, for example, oral, parenteral, topical, transdermal routes, such as, for example, subcutaneous, intravenous, intramuscular, intradermal, intraperitoneal, intraarterial, intrauterine, intraurethral, intracardial, intracerebral, intracerebroventricular, intrarenal, intrahepatic, intratendon, intraosseus, intrathecal, dermal, vaginal, rectal, inhalation, intranasal, ocular, auricular and buccal administration routes.

The administering may in addition comprise a technique or means such as electroporation, or sonication in order to assist in their delivery, for example transdermally. Other techniques which may be employed include for example, radio frequency or pressurized spray application.

The dosage administered will be dependent upon the age, health, and weight of the subject, the use of concurrent treatment, if any, frequency of treatment, and the nature of the effect desired. The amount of the isolated acidic fraction of mastic gum of the present invention in any unit dosage form comprises a therapeutically effective amount which may vary depending on the recipient subject, route and frequency of administration.

In general, the amount of the isolated acidic fraction of mastic gum present in the pharmaceutical composition may conveniently be in the range from about 0.01% to about 50%, such as, 0.01% to about 25%, such as 0.01% to about 12%, on a weight per weight basis, based on the total weight of the composition. For topical use, the percentage of the isolated acidic fraction of mastic gum in the composition may be in the range from about 0.05% to about 2.5%. For administration by injection, the percentage of the isolated acidic fraction of mastic gum in the composition may be conveniently in the range from about 0.1% to about 7%. For oral administration, the percentage of the isolated acidic fraction of mastic gum in the composition may be in the range from about 0.005% to about 7%.

In exemplary embodiments, the amounts of masticadienoic acid and isomasticadienoic acid in compositions consisting of these two compounds as the active ingredients may be in the range of about 0.05% to about 20% for each compound. For administration by injection, the amount for each may be in the range from about 0.1% to about 10%. For topical administration, the amount for each may be in the range from about 0.5% to about 12%. For oral administration, the amount for each may be in the range from about 0.5% to about 15%.

In exemplary embodiments, the amount of oleanonic acid, masticadienoic acid and isomasticadienoic acid in compositions consisting of these three compounds as the active ingredients may be in the range of about 0.05% to about 15% for each compound. For administration by injection, the amount for each may be in the range from about 0.1% to about 10%. For topical administration, the amount for each may be in the range from about 0.5% to about 12%. For oral administration, the amount for each may be in the range from about 0.5% to about 15%.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes. Pharmaceutical compositions for oral use may be obtained by combining the active compounds with solid and semi-solid excipients and suitable preservatives, and/or antioxidants. Optionally, the resulting mixture may be ground and processed. The resulting mixture of granules may be used, after adding suitable auxiliaries, if necessary, to obtain tablets, softgels, capsules, or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical compositions for oral use include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Other pharmaceutical compositions for oral use include a film designed to adhere to the oral mucosa, as disclosed for example in U.S. Pat. Nos. 4,713,243; 5,948,430; 6,177,096; 6,284,264; 6,592,887, and 6,709,671.

Pharmaceutical compositions in the form of suppositories consist of a combination of the active compound(s) with a suppository base. Suitable suppository bases include for example, natural or synthetic triglycerides, polyethylene glycols, or paraffin hydrocarbons.

Formulations for parenteral administration include suspensions and microparticle dispersions of the active compounds as appropriate. In some embodiments, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

Pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976) and in U.S. Pat. No. 7,048,943.

Formulations for topical administration include ointments. Suitable carriers include vegetable or mineral oils, white petrolatum, branched chain fats or oils, animal fats and waxes. The preferred carriers are those in which the active ingredient is soluble. Stabilizers, humectants and antioxidants may also be included, as well as agents imparting color or fragrance, if desired. Ointments may be formulated for example, by mixing a solution of the active ingredient in a vegetable oil such as almond oil with warm soft paraffin, and allowing the mixture to cool.

The pharmaceutical composition may comprise an oil-in-water emulsion or microemulsion in order to facilitate its formulation for oral, parenteral or topical use Such emulsions/microemulsions generally include lipids, surfactants, optionally humectants, and water. Suitable lipids include those generally know to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide. Suitable humectants, if used, include for example propylene glycol or polyethylene glycol.

The pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

The pharmaceutical composition may be formulated in the form of a cement such as those comprising polymethylmetacrylate (PMMA) or calcium phosphate, as are used in orthopedic surgery.

The pharmaceutical composition may be formulated in the form of a powder, in particular such as those used for transdermal applications using radio frequency, as described for example, in U.S. Pat. Nos. 6,074,688 and 6,319,541 and WO 2006/003659.

The pharmaceutical composition may be formulated in the form of a glue, such as those comprising octocyanoacrylate used for wound closure applications.

Therapeutic Uses

The present invention provides therapeutic uses and methods of treating impaired neurological function, treating skin and scalp disorders, inducing tissue repair and wounds in a subject in need thereof. The methods comprise administering to the subject a therapeutically effective amount of a composition comprising an isolated acidic fraction of mastic gum, as described herein. In some embodiments, the method comprises administering to the subject a therapeutically effective amount of a composition comprising a combination of at least two triterpenoic acids selected from: masticadienolic acid; isomasticadienolic acid; isomasticadienolic acid; 3-O-acetyl masticadienolic acid; 3-O-acetyl epimasticadienolic acid; 3-O-acetyl isomasticadienolic acid, 3-O-acetyl epi-isomasticadienolic acid; and oleanonic acid. In further embodiments, the method comprise administering to the subject a therapeutically effective amount of a composition comprising a combination of at least two triterpenoic acids selected from masticadienoic acid; isomasticadienoic acid and oleanonic acid.

In some embodiments, the method comprises administering to the subject a therapeutically effective amount of a composition comprising triterpenoic acids consisting of masticadienoic acid and isomasticadienoic acid. In further exemplary embodiments, the method comprises administering to the subject a therapeutically effective amount of a composition comprising triterpenoic acids consisting of oleanonic acid, masticadienoic acid and isomasticadienoic acid.

The step of administering the compositions may comprise any acceptable route including oral, topical, parenteral, and transdermal, such as, for example, parenteral administration includes intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus, intrathecal, dermal, vaginal, rectal, inhalation, intranasal, ocular, auricular and buccal routes of administration.

In some embodiments, the step of administering comprises contacting cells of a particular type, of a particular lineage or at a particular stage of differentiation, with the composition. The cells may be any of a wide variety of cell types, including in particular, neural cells, neuronal cells, endothelial cells, epithelial cells and stem cells of said lineages. Further, the cells may be of any lineage for example, ectodermal, mesodermal, entodermal lineages and stem cells of said lineages. In various embodiments, the step of contacting cells is carried out in vivo, ex vivo or in vitro. In some embodiments, the cells to be contacted are stem cells and the contacting of the cells is carried out in vivo, ex vivo and in vitro. In some embodiments, the stem cells are contacted in vivo. In some embodiments, the stem cells are contacted ex vivo. In some embodiments, the stem cells are contacted in vitro.

The method disclosed herein for treating impaired neurological function is particularly advantageous for subjects afflicted with neurodegenerative conditions and diseases, including in particular, trauma, stroke, vascular dementia, senile dementia, Alzheimer's disease, amyotrophic lateral sclerosis (ALS), multiple sclerosis (MS), and Parkinson's disease.

In other cases, the method may be applied in subjects suffering from impaired neurological function due to an infection (e.g. viral, bacterial, fungal, parasitic).

In some embodiments the method may be applied in subjects suffering from impaired neurological function due to an immunological disorder.

In some embodiments, the impaired neurological function is due to exposure to a drug, such as an anesthetic.

In some embodiments, impaired neurological function may also be associated with a condition selected from the group consisting of schizophrenia, bipolar disorder, depression, obesity, anorexia and cachexia.

In some embodiments, skin and scalp disorders include all disorders of skin, scalp and hair appendages, including for example, nails and hair follicles. Particular conditions that may benefit from the invention include alopecia, eczema, psoriasis, seborrheic keratosis, seborrhea and skin wounds. Skin wounds include venous leg ulcers, pressure ulcers, diabetic foot ulcers, burns, amputation wounds, decubitus ulcers (bed sore), split-skin donor grafts, skin graft donor sites, medical device implantation sites, bite wounds, frostbite wounds, puncture wounds, shrapnel wounds, dermabrasions, contusions, an infection wounds and surgical wounds. Wounds may be the result of infection; exposure to ionizing radiation; exposure to laser, or exposure to a chemical agent.

In some embodiments, the invention may be effective and economical for treatment of chronic non-healing wounds. As is known to one of ordinary skill in the art, the efficacy of a particular treatment in promoting wound healing may be assessed by various criteria, including the rate of closure measured by length, width and depth of the wound over time, epithelization rate, formation of granulation tissue and tissue tensile strength.

In some embodiments, the invention may be particularly effective for inducing and promoting life span extension in humans, non-human mammals, birds and fish.

In some embodiments, the methods disclosed herein for inducing or promoting tissue regeneration are particularly advantageous for subjects who have tissue damage, which for example, may be associated with, or the result of an injury or insult. The methods for inducing or promoting tissue regeneration may be used in subjects who have suffered an injury or insult selected from the group consisting of a myocardial infarction, a pulmonary embolism, a cerebral infarction, peripheral artery occlusive disease, a hernia, a splenic infarction, a venous ulcer, an axotomy, a retinal detachment, a wound (for example, a burn wound, bite wound, a frostbite wound, a puncture wound, a shrapnel wound, a contusion, an infection wound or a surgical wound), an infection and a surgical procedure. In some embodiments, the invention may be effective for scar-less repair of wounds.

In some embodiments, the method may be carried out prior to or following implantation of a medical device into the subject. Medical devices include, but are not limited to a prosthetic, an artificial organ or component thereof, a valve, a catheter, a tube, a stent, an artificial membrane, a pacemaker, a sensor, an endoscope, an imaging device, a pump, a wire and an implant. Implants include, but are not limited to a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the medical device is an organ implant, which may in certain cases comprise autologous cells of the subject.

In some embodiments, the step of contacting comprises a means selected from the group consisting of electroporation, sonication, radio frequency, pressurized spray and combinations thereof.

In some embodiments, the step of contacting comprises establishing contact between interstitial fluid and the composition. This may be particularly advantageous for wounds which are surrounded by interstitial fluid. Contact between interstitial fluid and the composition may be accomplished by piercing and/or teasing the dermis with a needle, a microneedle, or an apparatus comprising a plurality of needles or microneedles. Such needles or microneedles are preferably non-hollow and may be fashioned in a plurality for example, on a comb or brush-like apparatus.

The method of the invention is suitable for application in humans, non-human mammals, fish and birds.

Articles of Manufacture

The method of the invention may encompass use of an article of manufacture which incorporates the composition comprising the isolated acidic fraction of mastic gum described herein.

The pharmaceutical composition may be in the form of a coating on the article of manufacture, or may be contained within a vessel which is integral to the article of manufacture. The pharmaceutical composition is advantageously present as a coating on devices which are inserted to the body and are intended for integration therein, for example an implant. The pharmaceutical composition can thus promote tissue closure over the implant due to the activity of the isolated acidic fraction of mastic gum in inducing cell differentiation.

The pharmaceutical composition may be advantageously incorporated onto or into articles used in wound healing or tissue repair, for example, a dressing or bandage. The pharmaceutical composition can thus promote wound healing due to the activity of the isolated acidic fraction of mastic gum in inducing cell differentiation.

In other cases, the pharmaceutical composition may be incorporated to a delivery device such as a needle, an injection device or a spray dispenser from which the composition is delivered to a body site requiring therapy, for example a wound site.

Articles of manufacture include, but are not limited to a fabric article, a diaper, a wound dressing, a medical device, a needle, a microneedle, an injection device and a spray dispenser. In some embodiments, the article of manufacture comprises a plurality of microneedles. Medical devices and implants are as hereinbefore described.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1 Preparation of Isolated Acidic Fraction of Mastic Gum

Mastic resin (10 g) was combined with absolute ethanol (200 ml) and the mixture was allowed to stand overnight. The mixture was shaken at 150 rpm for ca. 15 minutes, leaving an insoluble gum on the bottom of the flask. Any larger insoluble particles were allowed to settle over 20 minutes, and the ethanol was transferred into a new flask. The remainder was shaken with a fresh portion of absolute ethanol (150 ml) at 200 rpm for 10 minutes. This ethanol fraction was combined with the first fraction. The procedure was repeated with another 150 ml portion of absolute ethanol which was combined with first two ethanol fractions. Subsequently, the ethanol was removed in vacuo using a rotary evaporator (water-bath temperature 30° C.). Hexane (300 ml) was added to the remaining residue and the mixture was shaken at 150 rpm for two hours. After standing overnight in the closed flask in order to complete dissolution of soluble material and precipitation of any insoluble material, the clear hexane solution was transferred into a clean pre-weighed flask and the hexane was removed using a rotary evaporator, yielding ca. 6 gram extracted material. The obtained extracted material was subsequently dissolved in diethyl ether (300 ML) and extracted with a 5% aqueous sodium carbonate solution (4×100 ML), followed by extraction with 0.1 N aqueous sodium hydroxide (3×100 ML). The two basic aqueous extracts were separately acidified to pH 1-2 by slow addition of 10% aqueous hydrochloric acid and subsequently extracted with fresh diethyl ether (3×100 ML). The thus obtained ether fractions were combined and dried over anhydrous sodium sulfate. After filtering off the sodium sulfate, the diethyl ether was removed using a rotary evaporator. This gave ca. 3 gram of isolated acidic fraction of mastic gum as a white solid.

For comparison, addition of hexane to the acidic fraction as prepared according to the teaching of WO2003/092712 or Parachos et al, (2007), Antimicrobial Agents and Chemotherapy, 51(2), 551, showed that a substantial amount of that acidic fraction was insoluble in hexane. When this hexane-insoluble material was tested in the in vitro assay described in Example 4 as a 1% ethanolic solution (it was found to be largely insoluble in cottonseed oil), it was found to cause severe stress to the cells. Plane ethanol was used as negative control and did not cause any stress or harm to the cells at the used volumes. In addition, a 1% ethanolic solution of the acidic fraction prepared according to the current invention induced efficient differentiation of the cells into neuronal cells. This result clearly indicates that the acidic fraction of the current invention is free of detrimental material which is present in acidic fractions disclosed in the prior art.

Example 2. Preparation of a 5% (w/w) Composition of Isolated Acidic Fraction of Mastic Gum in USP/NF Grade Cottonseed Oil (RPh-Ac)

To 1 gram of the obtained isolated acidic fraction from Example 1 was 19 grams of cottonseed oil (USPINF) was added and the mixture was shaken at 150 rpm until a clear and homogeneous composition was obtained (ca. 2 hours).

Example 3. Isolation and Chemical Characterization of Isolated Acidic Fraction of Mastic Mastic resin from *Pistacia lentiscus* L. was extracted according to Example 1 to obtain the fraction which was analyzed by reversed phase HPLC (FIG. 1) in order to identify the major constituents. The HPLC analysis is consistent with the presence the isolated fraction of moronic acid and oleanonic acid in the isolated fraction, on the basis of comparison with analytical standards.

The conditions used for reversed phase HPLC method of the isolated acidic fraction were: Flow rate: 1 ml/min; detection UV wavelength 220 nm; sample concentration 1 mg/ml; injection volume 20 µl; needle and pump back washed with 20% aqueous acetonitrile; ELSD—nitrogen flow 1 ml/min; evaporation temperature −80° C.; nebulization temperature 60° C.; 0.8% Acetic acid-ACN gradient. Gradient ratio for acidic substance and formulation samples is shown in Table 1:

TABLE 1

| time | A - 0.8% Acetic acid | B - ACN |
|------|----------------------|---------|
| 0    | 20                   | 80      |
| 5    | 20                   | 80      |
| 25   | 7.7                  | 92.3    |
| 45   | 8                    | 92      |
| 48   | 0                    | 100     |
| 55   | 0                    | 100     |
| 57   | 20                   | 80      |
| 67   | 20                   | 80      |

Mass spectral data of the isolated acidic fraction (FIGS. 2A-D and FIG. 3A) show peaks indicating the presence of monomeric triterpenic acids such as moronic acid, oleanonic acids and others (MH$^+$ at 455 Da; M$^+$+Na at 477 Da. Also present in the mass spectral data are peaks corresponding to dimeric triterpenoic acids (MH$^+$ at 910 Da; M$^+$+Na at 932

Da), as well as peaks indicative of trimeric forms of triterpenoic acids (MH+ at 1364 Da; M++Na at 1387).

In order to isolate and determine the structure of further main constituents of the isolated acidic fraction, a preparative HPLC method was developed. Using this method, six major constituents of the isolated acidic fraction were subsequently isolated by preparative HPLC.

A preparative HPLC method was developed on a 30×250 mm preparative column (ACE-121-2530). Samples of the isolated fraction (ca. 75 mg per run) were injected using a 5 ML loop.

Method Details:
Detection wavelength: 205 nm; Flowrate: 15 ml/min
Eluents:
1. 0.8% acetic acid:acetonitrile:THF=25:72:3
2. 0.8% acetic acid:acetonitrile:THF=15:82:3
3. 0.8% acetic acid:acetonitrile:THF=10:87:3
4. 0.8% acetic acid:acetonitrile:THF=5:92:3

Schedule: Prior to conditioning of column, it has to be washed with Acetonitrile HPLC grade during at least 40 minutes. The total run time is ca. 155 minutes.
Conditioning: Run Eluent 1 for 30 mins.
Load: Inject 5 ML solution of 75 mg sample in MeOH
Elution:
Eluent 1: 0-10 minutes
Eluent 2: up to elution of peak 2
Eluent 3: until 10 minutes after elution of peak 4
Eluent 4: until 10 minutes after elution of peak 6

Figure 4:
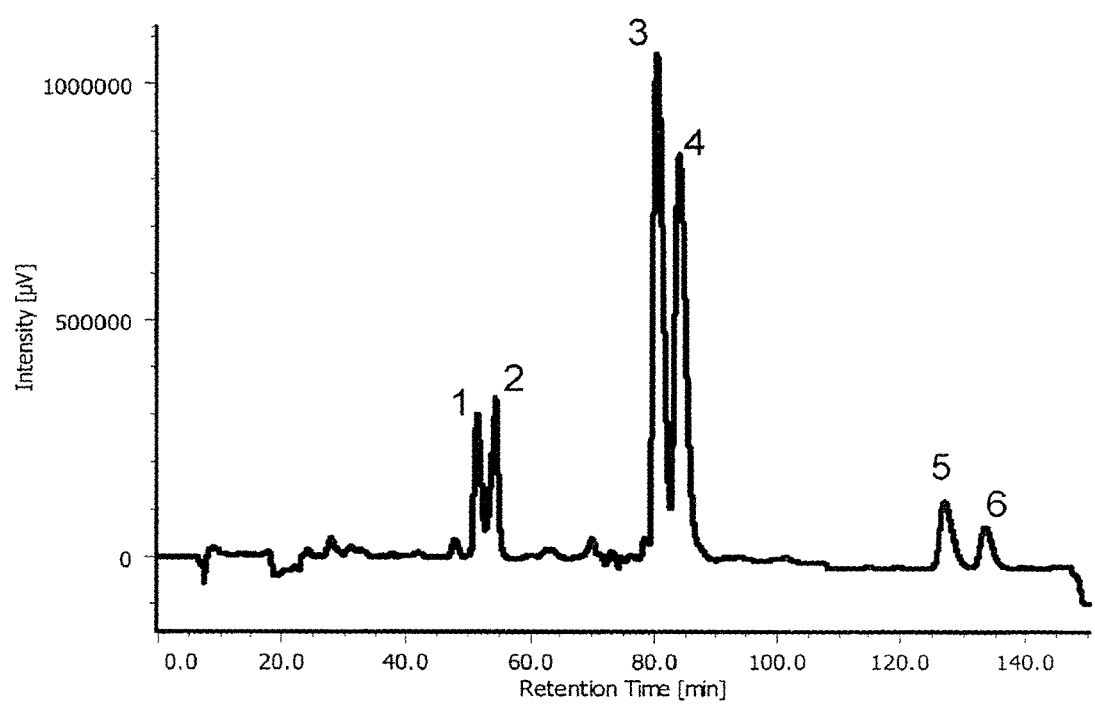
FIG. 4 shows that preparative chromatogram of the isolated acidic fraction as prepared according to Example 1. The peak numbering corresponds with the peak numbering of the analytical chromatogram of FIG. 1.

The chromatogram of the preparative HPLC method is shown in FIG. 4.

The compounds corresponding to the six indicated peaks in FIG. 4 were isolated and characterized by $^1$H-NMR and $^{13}$C-NMR.

Figure 5A:
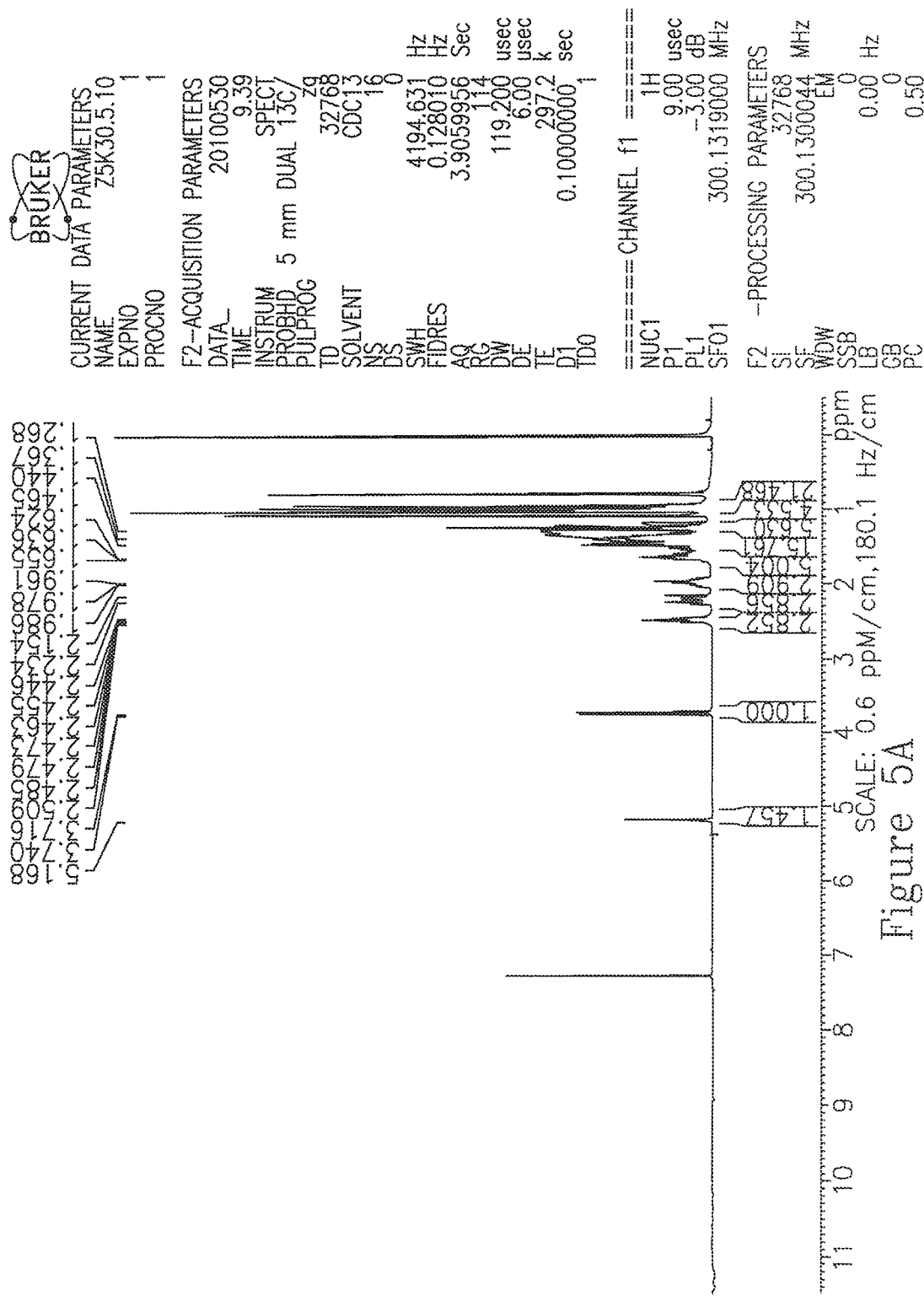
FIG. 5A shows the $^1$H-NMR spectrum of moronic acid, isolated by preparative HPLC from the acidic fraction prepared according to Example 1.
Figure 5B:
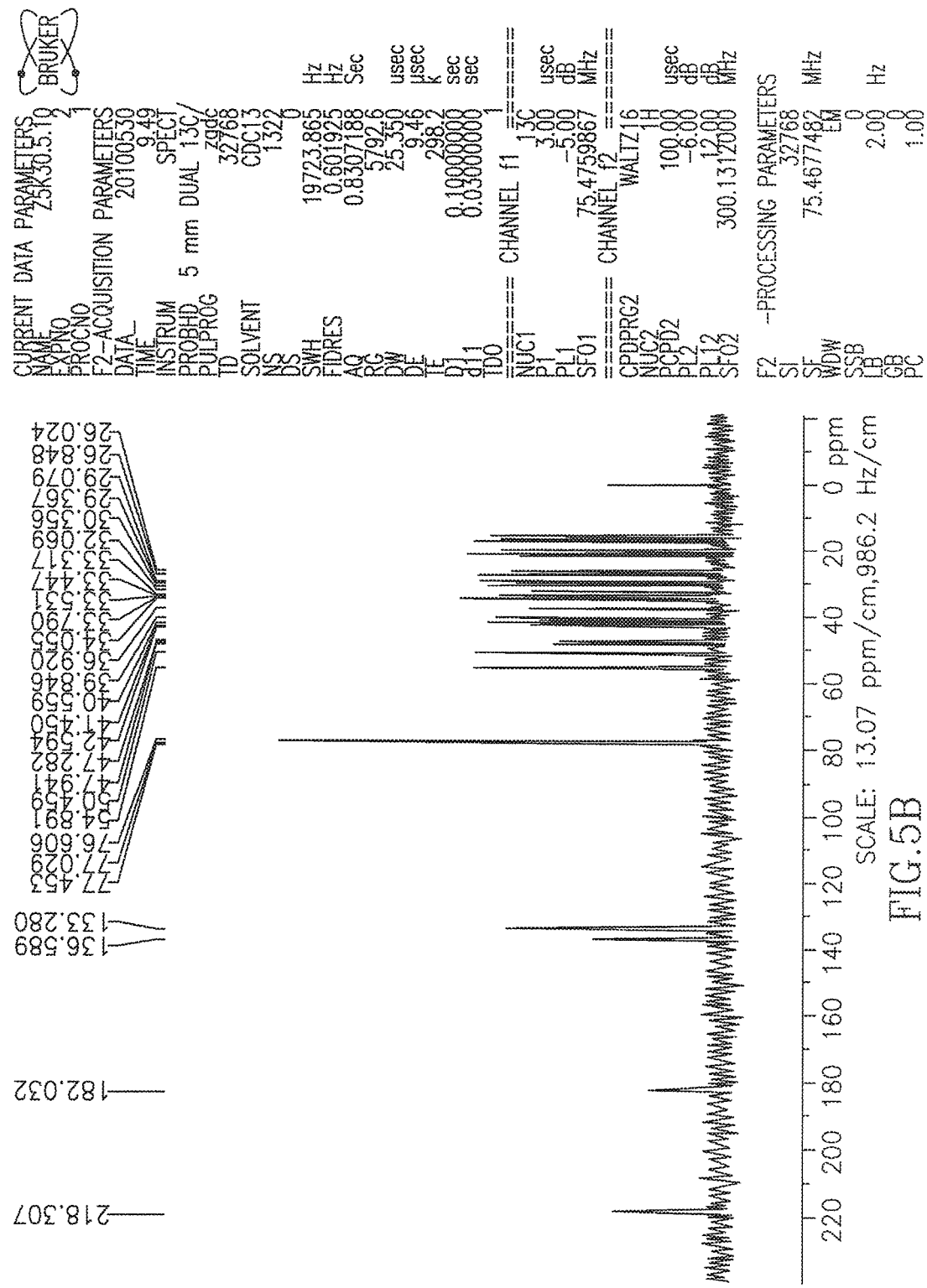
FIG. 5B shows the $^{13}$C-NMR spectrum of moronic acid, isolated by preparative HPLC from the acidic fraction prepared according to Example 1.
Figure 6A:
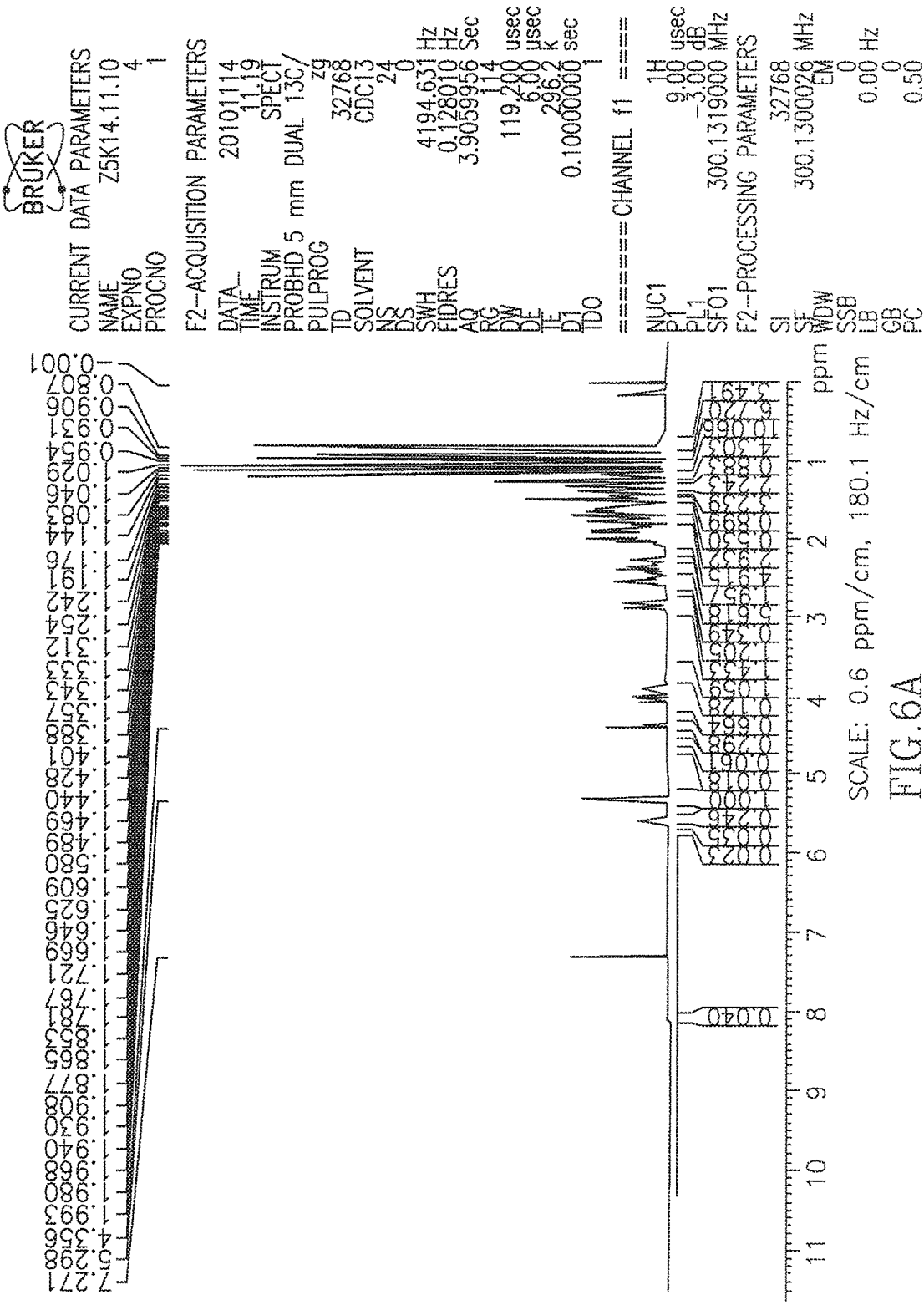
FIG. 6A shows the $^1$H-NMR spectrum of oleanonic acid, isolated by preparative HPLC from the acidic fraction prepared according to Example 1.
Figure 6B:
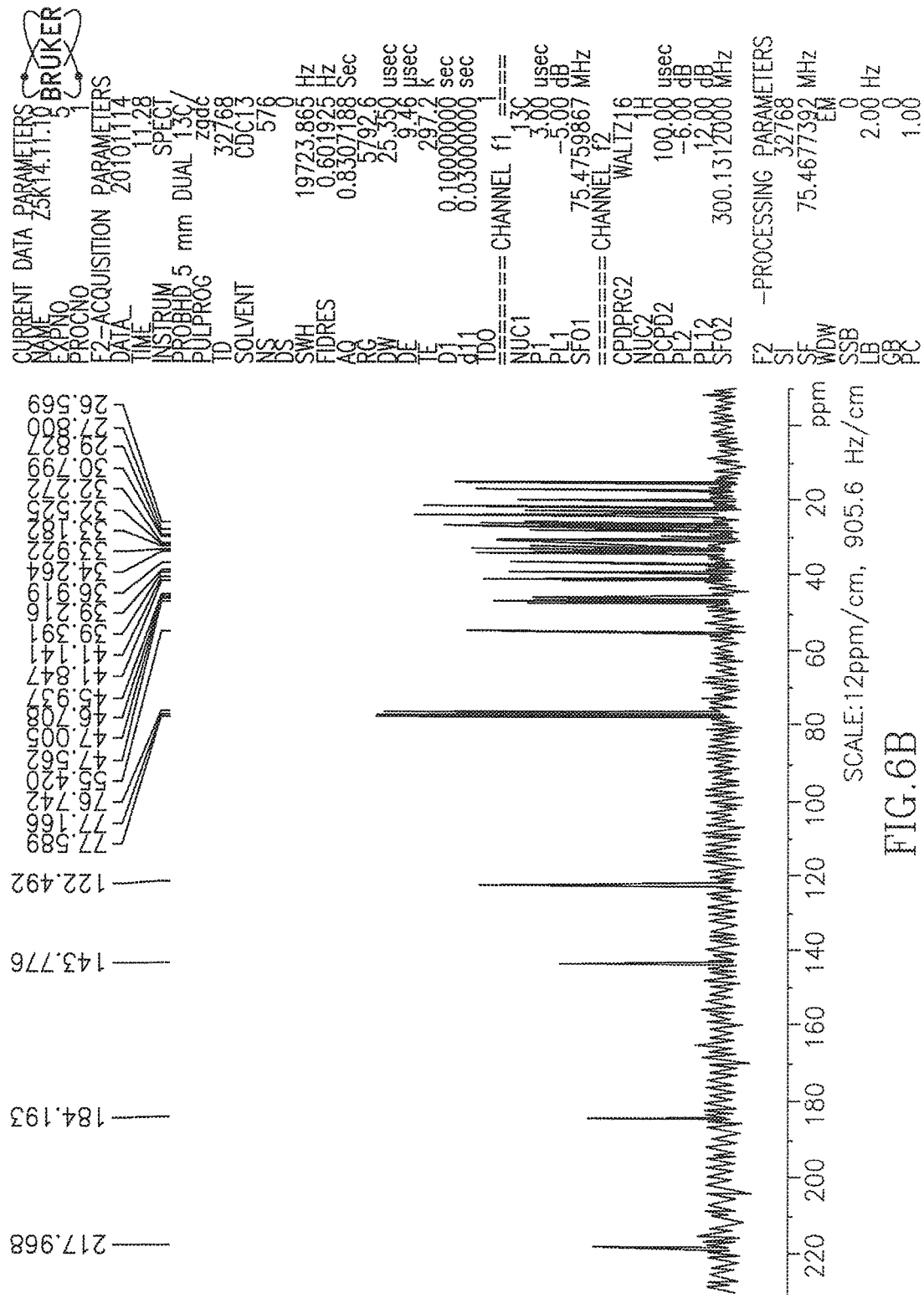
FIG. 6B shows the $^{13}$C-NMR spectrum of oleanonic acid, isolated by preparative HPLC from the acidic fraction prepared according to Example 1.
Figure 7A:
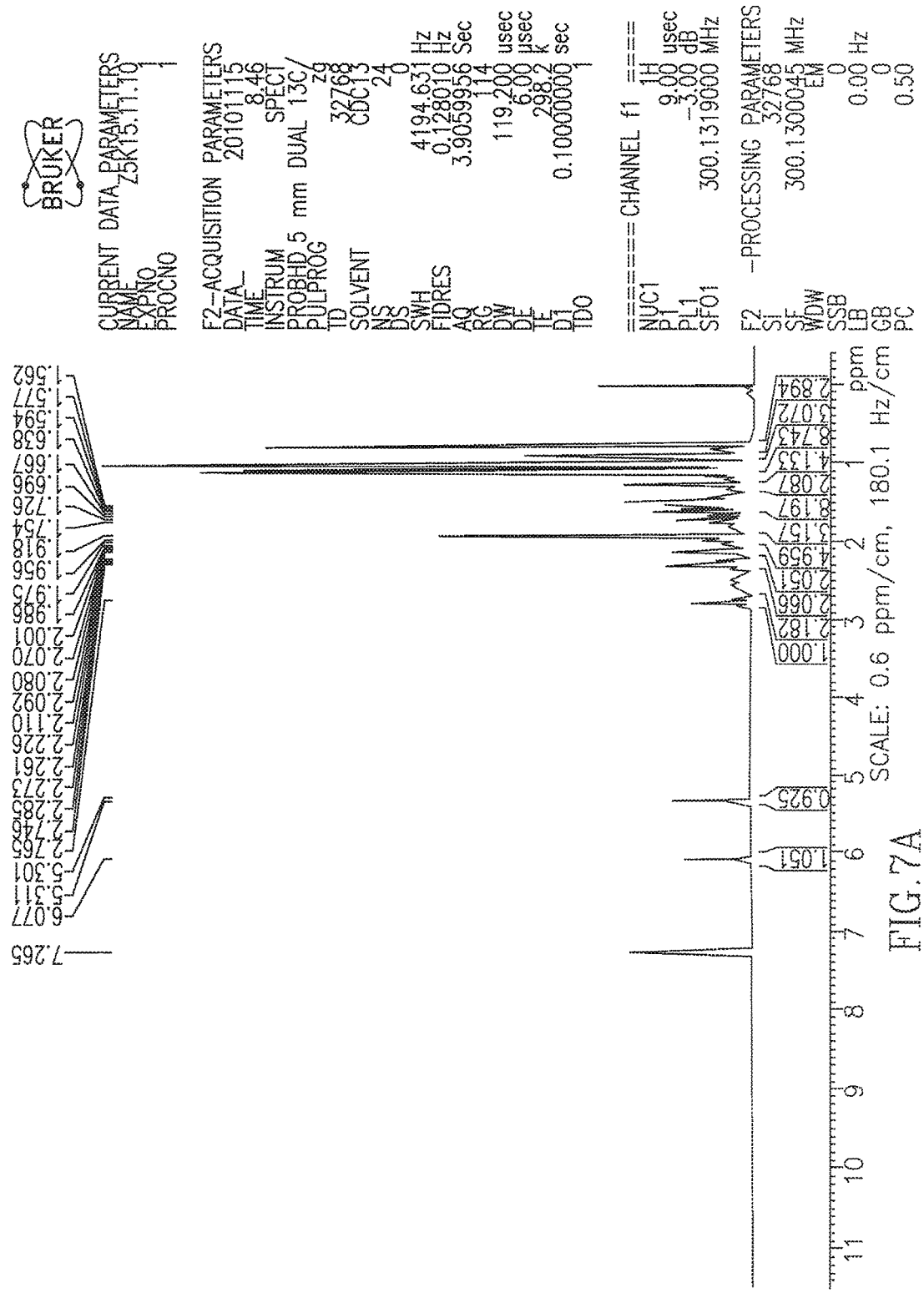
FIG. 7A shows the $^1$H-NMR spectrum of masticadienoic acid, isolated by preparative HPLC from the acidic fraction prepared according to Example 1.
Figure 7B:
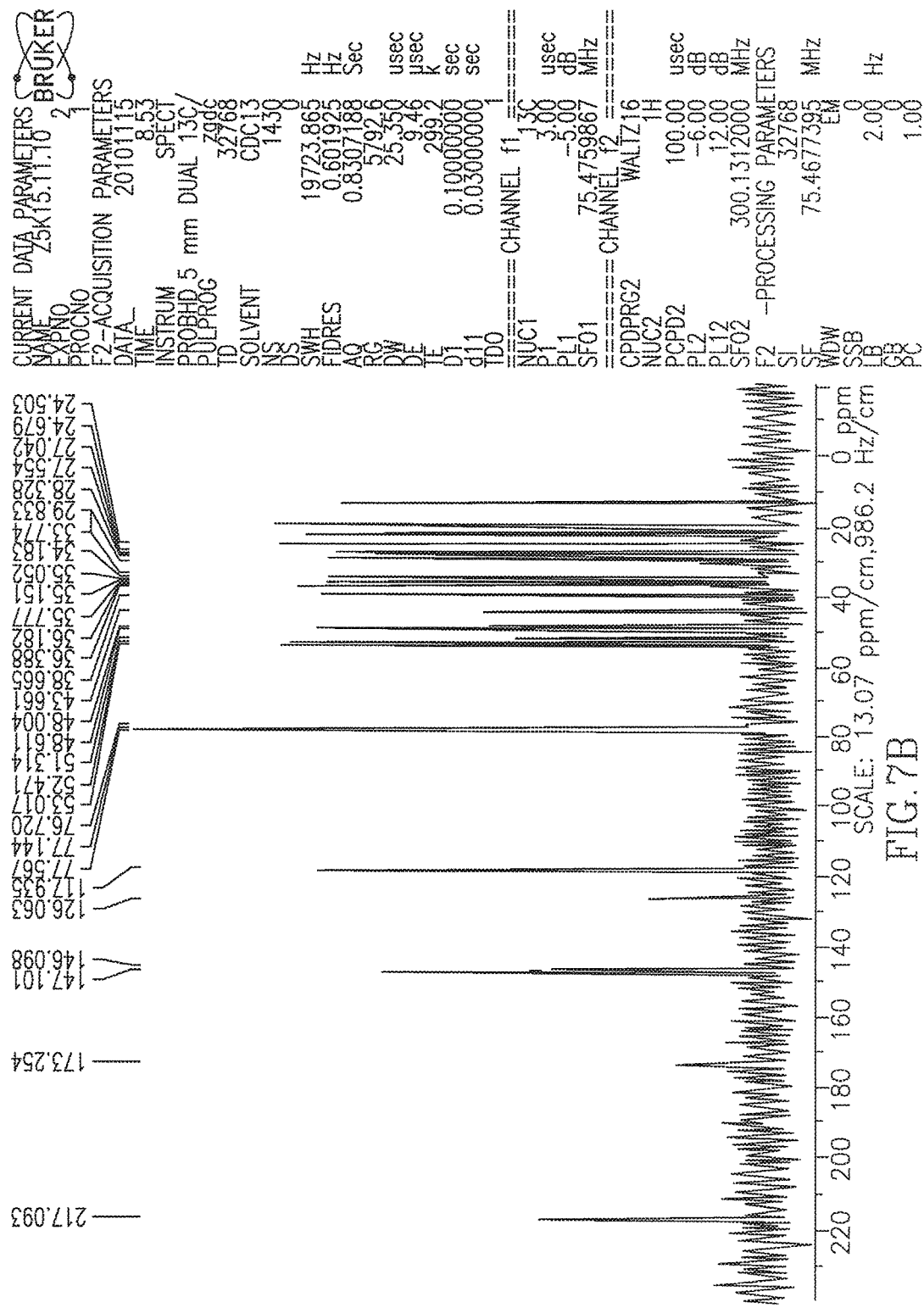
FIG. 7B shows the $^{13}$C-NMR spectrum of masticadienoic acid, isolated by preparative HPLC from the acidic fraction prepared according to Example 1.
Figure 8A:
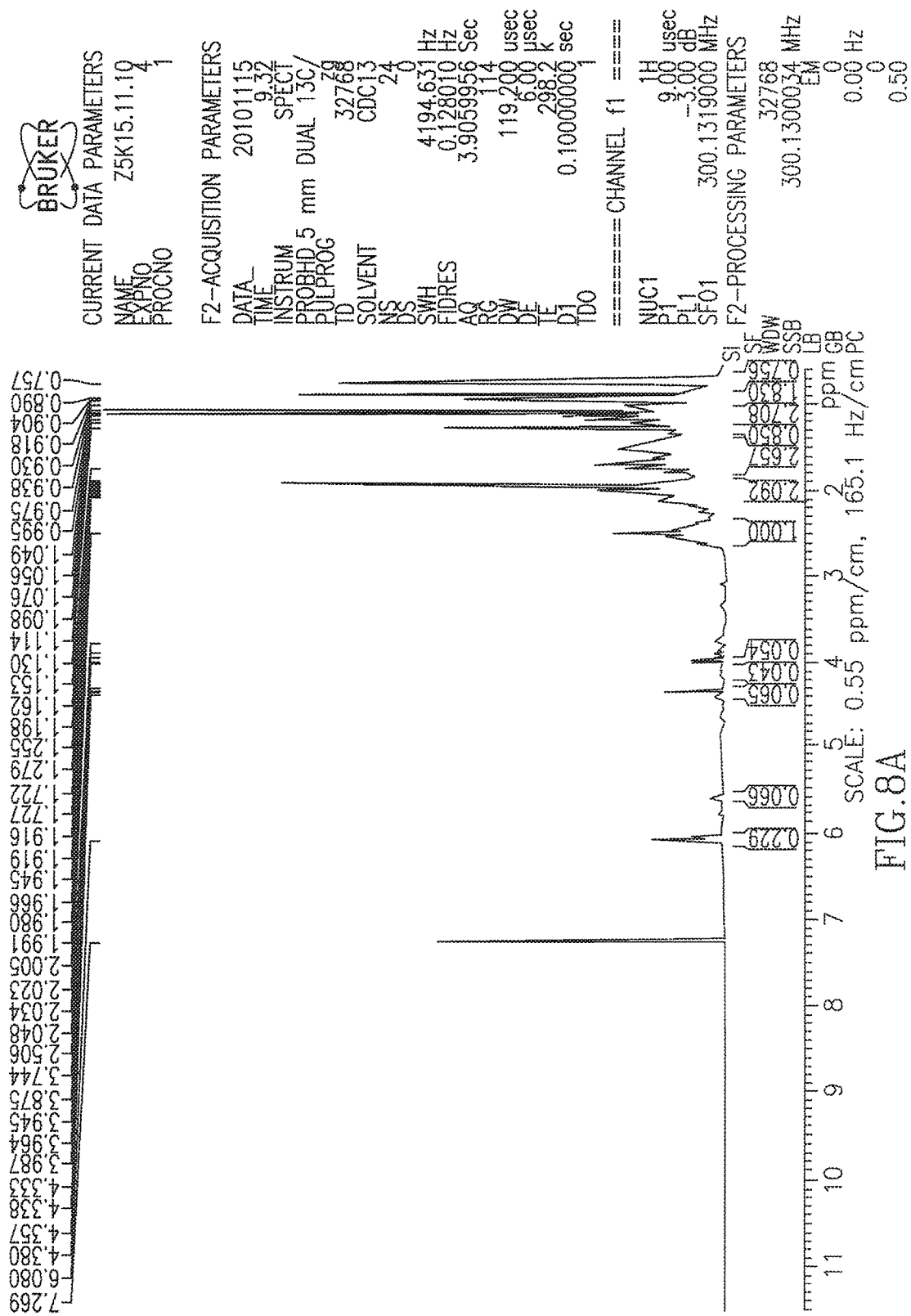
FIG. 8A shows the $^1$H-NMR spectrum of isomasticadienoic acid, isolated by preparative HPLC from the acidic fraction prepared according to Example 1.
Figure 8B:
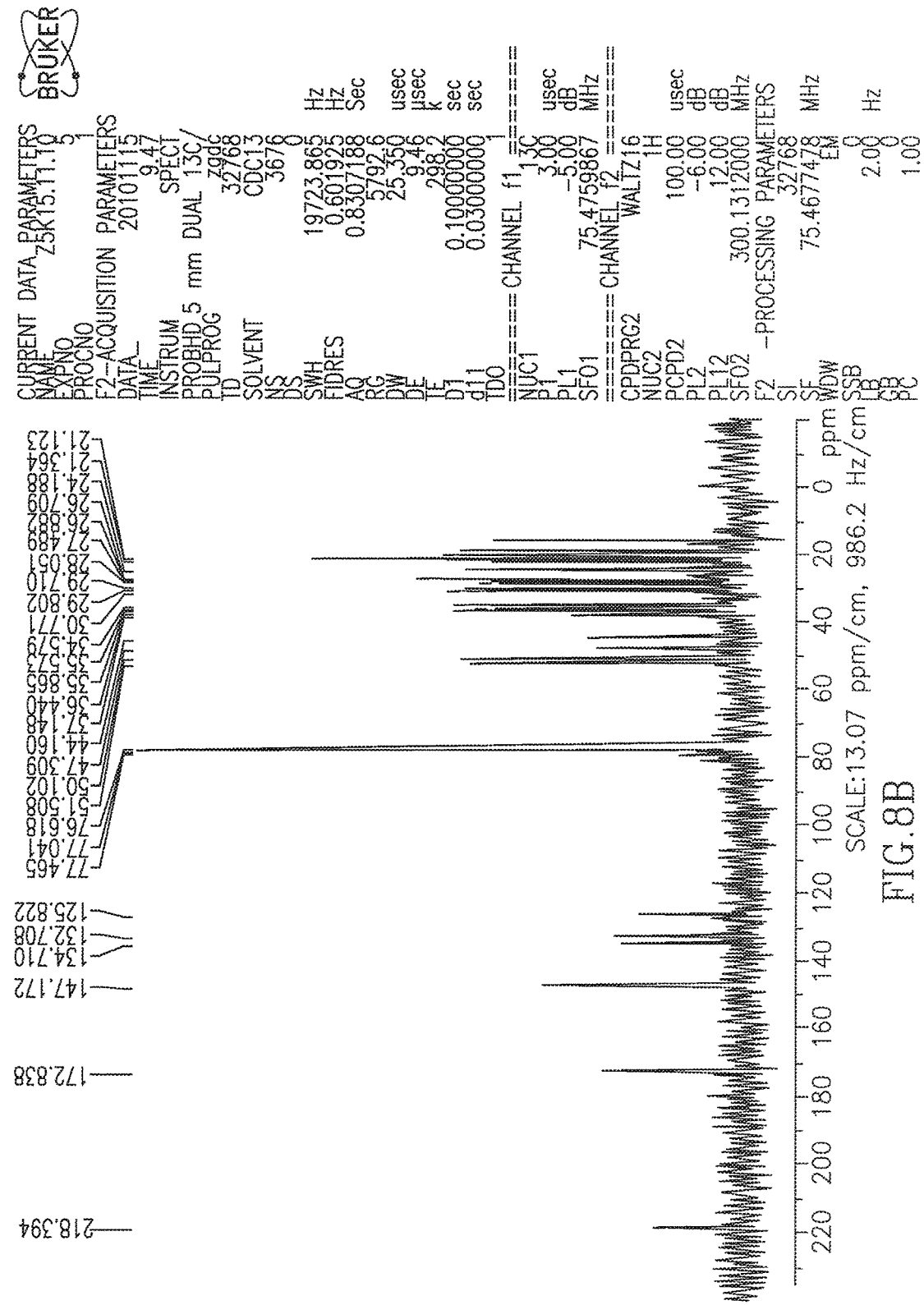
FIG. 8B shows the $^{13}$C-NMR spectrum of isomasticadienoic acid, isolated by preparative HPLC from the acidic fraction prepared according to Example 1.
Figure 9A:
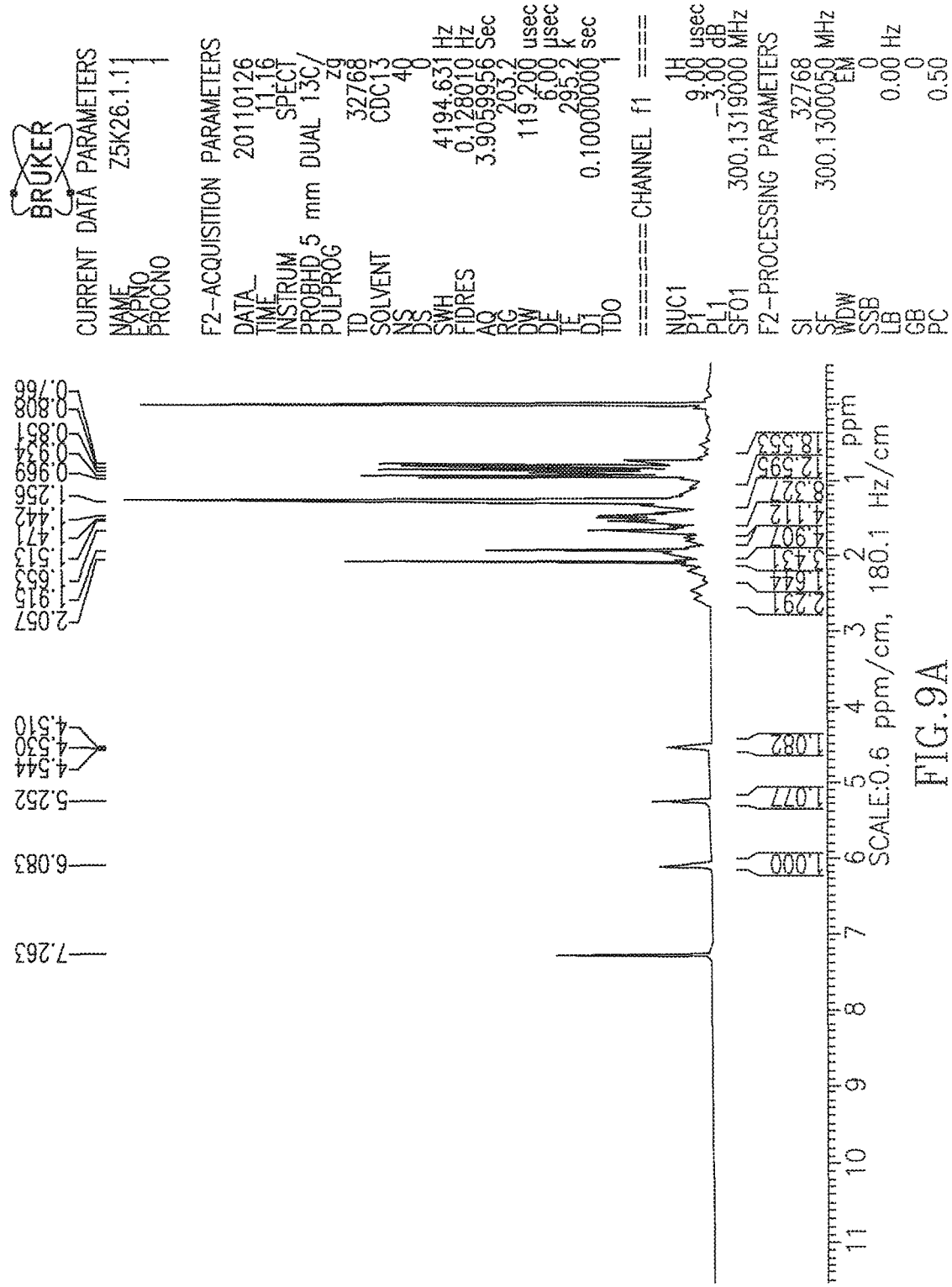
FIG. 9A shows the $^1$H-NMR spectrum of 3-(O-Acetyl)-masticadienolic acid, isolated by preparative HPLC from the acidic fraction prepared according to Example 1.
Figure 9B:
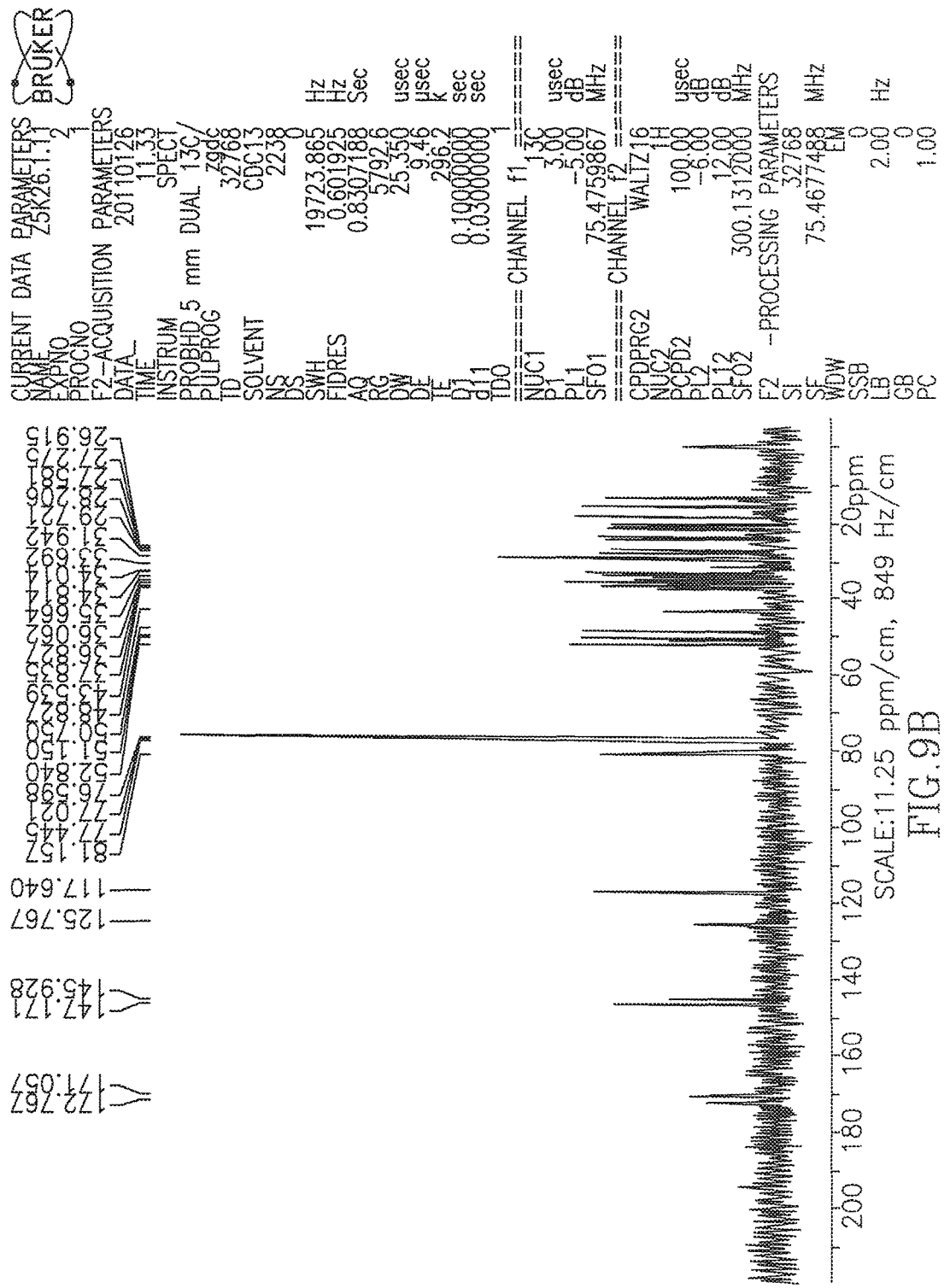
FIG. 9B shows the $^{13}$C-NMR spectrum of 3-(O-Acetyl)-masticadienolic acid, isolated by preparative HPLC from the acidic fraction prepared according to Example 1.
Figure 10A:
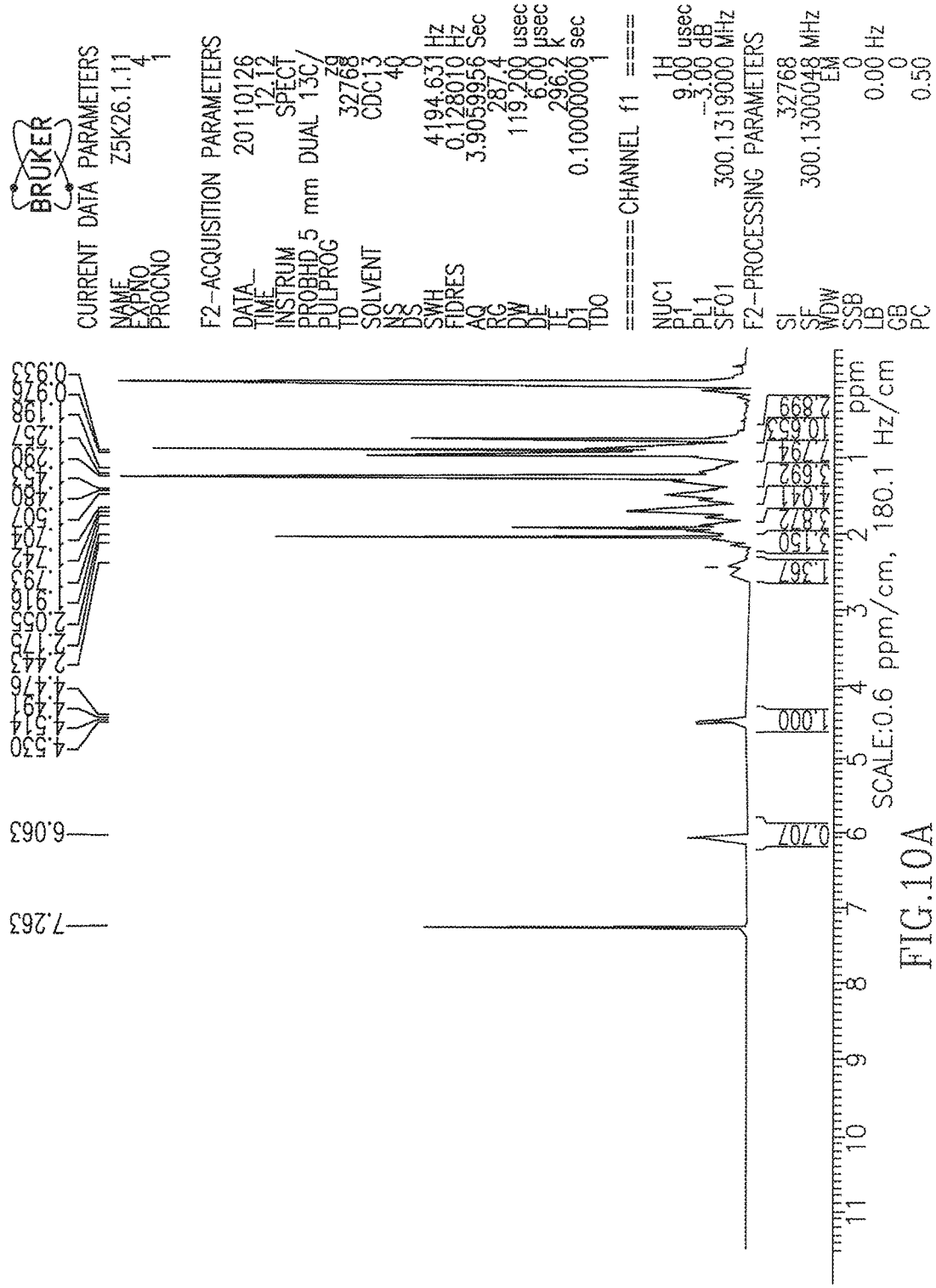
FIG. 10A shows the $^1$H-NMR spectrum of 3-(O-Acetyl)-isomasticadienolic acid, isolated by preparative HPLC from the acidic fraction prepared according to Example 1.
Figure 10B:
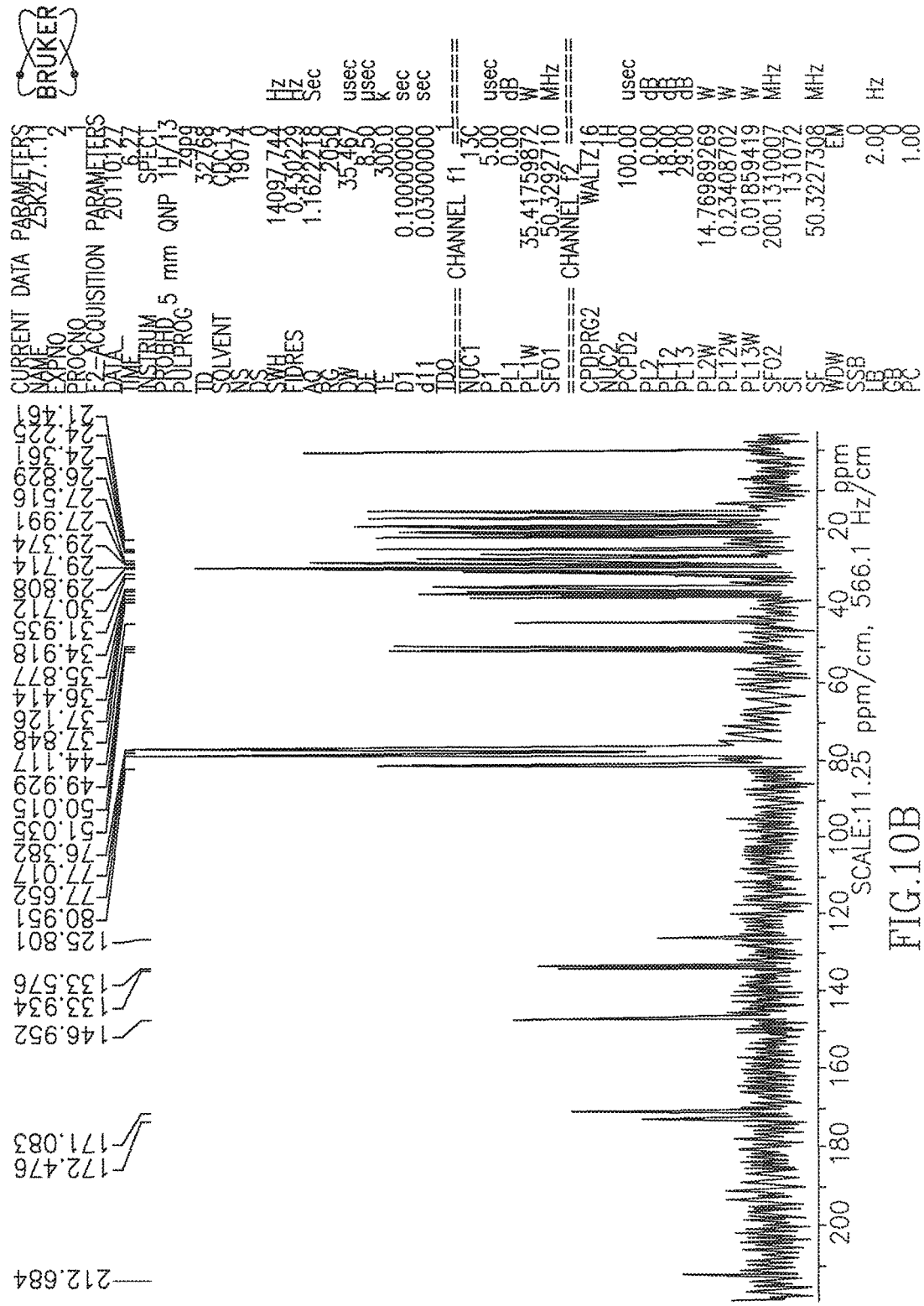
FIG. 10B shows the $^{13}$C-NMR spectrum of 3-(O-Acetyl)-isomasticadienolic acid, isolated by preparative HPLC from the acidic fraction prepared according to Example 1.

Peak 1 and peak 2 were indeed shown to be respectively moronic acid and oleanonic acid upon comparison of the NMR spectra with literature data. The $^1$H-NMR and $^{13}$C-NMR spectra of these two acids are shown in FIGS. 5A-B (Peak 1, moronic acid) and 6A-B (Peak 2, oleanonic acid), respectively. Moronic acid was also positively identified by comparison with a commercial sample. Oleanonic acid was further compared and found to be identical with, a sample prepared by oxidation of oleanolic acid according to a literature method (Helv. Chim. Acta Vol. 83, p. 1766 (2000).

Peaks 3-6 were shown to be masticadienoic acid (peak 3), isomasticadienoic acid (peak 4), 3-OAcetyl-masticadienolic acid (peak 5) and 3-O-acetyl-isomasticadienolic acid (peak 6), respectively. The $^1$H-NMR and $^{13}$C-NMR spectra of these is shown in FIGS. 7A-B, FIGS. 8A-B, FIGS. 9A-B and FIGS. 10A-B, respectively. (For reference—Parachos et al, (2007), Antimicrobial Agents and Chemotherapy, 51(2), 551 and references therein.)

Example 4. Biological Studies of RPh-Ac in Retinal Pigment Epithelium (RPE) Cells Studies aimed at evaluating effects of RPh-Ac on various cell lines of human origin led to use of ARPE-19 cells, a non-malignant human retinal pigment epithelial cell line.

The retinal pigment epithelium (RPE) is a single layer of hexagonal pigmented epithelial cells of neuronal origin, which forms the outermost cell layer of the eye retina and is attached to the underlying choroid. RPE functions include support, nourishment and protection of the underlying photoreceptors of the neuro-retina.

ARPE-19 cells are involved in the phagocytosis of the outer segment of photoreceptor cells, in the vitamin A cycle, where they isomerize all-trans retinol to 11-cis retinal and in supplying the photoreceptors with D-glucose, amino acids and ascorbic acid.

Although in vivo the RPE is pigmented, ARPE-19 cells do not form melanin and are not pigmented. In culture the cells grow as spindle shaped and as polygonal cells.

Methods

ARPE-19 cells (obtained from the American Type Culture Collection, (ATCC)) were plated in flat bottom 96 well tissue culture microplates (Costar) at a concentration of 2-5×10$^3$ cells per well (1-2.5×10$^4$ cells/mL) in a growth medium consisting of DMEM:Ham F-12, 1:1, supplemented with 10% Fetal Bovine Serum, 200 mM glutamine, 100 units/mL penicillin and 100 μg/mL streptomycin. The cells were allowed to adhere to the plate surfaces overnight prior to treatment with RPh-Ac.

RPh-Ac was prepared essentially as described in Example 2, to provide a 2.5% solution in a carrier composed of cottonseed oil. The preparations were added to the wells at volumes of 0.5 μl, 1 μl, 1.5 μl, 2 μl. These volumes, introduced into an overall sample medium volume of 200 μl, correspond to final RPh-Ac concentrations of 0.0125%, 0.025%, 0.0375% and 0.05%, respectively. The oil carrier served as a vehicle control and was applied to control cultures at the same volumes.

The cultures were incubated in a 37° C., 5% CO$_2$ incubator for 48 hrs. The medium was then removed, the cultures washed twice with phosphate buffered saline (PBS), fixed with absolute methanol for 10 min and stained with Hemacolor® reagents (Boehringer Mannheim), which stain cells in a manner similar to Giemsa, and may be used in a quantitative cell viability assay (Keisari, Y. A colorimetric microtiter assay for the quantitation of cytokine activity on adherent cells in tissue culture. J. Immunol. Methods 146, 155-161, 1992).

To determine the expression of marker proteins, Synaptophysin, phosphorylated Akt (pAkt$^{Ser473}$) and phosphorylated GSK3-beta$^{Ser9}$) in response to treatment of the cells with RPh-Ac, cells were plated on sterile glass coverslips immersed in 24 well microplates at a concentration of 5·10$^4$ cells/well in a medium consisting of 1:1 mixture of Dulbecco's minimal essential medium (DMEM) and Ham F12 medium, supplemented with 10 fetal bovine serum and penicillin (100 units/ml), streptomycin (100 μg/ml) and glutamine (2 mM).

The cells were allowed to adhere overnight to cover slips and 2.5% RPh-Ac in cottonseed oil was added to the culture at a volume of 20 μl/ml medium and incubated in a 37° C., 5% CO$_2$ for 48 hrs. The oil carrier served as a vehicle control and was applied to control cultures at the same volume.

The cells were then washed 2× with PBS and fixed with 4% paraformaldehyde. To determine protein expression of, Synaptophysin, pAkt$^{Ser473}$, and phosph-GSK3-beta$^{Ser9}$ in the cells, the glass coverslips were stained with mouse/rabbit monoclonal antibodies (Ab.) direct against human Synaptophysin, pAkt$^{Ser473}$, and pGSK3-beta$^{Ser9}$, followed by secondary FITC-labeled anti-mouse/rabbit IgG. The cells nuclei were counter stained with DAPI. Test and control preparation were then evaluated in a fluorescence microscope. The results are presented in FIGS. 13A-C, herein below.

Results

Treatment of ARPE-19 RPE cells with RPh-Ac was unexpectedly found to induce dramatic morphological changes that are unequivocally characteristic of neuro-differentiation. The morphological changes did not occur in control cultures treated with oil carrier alone, and similar results were seen among the test cultures treated with RPh-Ac, regardless of the oil used as the carrier for the active compound. The morphological changes were also associated with cessation in cell proliferation, further supporting the conclusion that RPh-Ac induces neuro-differentiation.

Figure 11A:
FIG. 11A shows the effect of the acidic fraction prepared according to the teaching of WO 2003/097212 on ARPE-19 cells.
Figure 11B:
FIG. 11B shows the effect of the acidic fraction prepared according to Example 2 of the current invention on ARPE-19 cells.

Control oil-treated cultures displayed the typical spindle shaped and polygonal growth pattern characteristic of ARPE-19 RPE cells (FIG. 11A). After 48 hours of incubation in culture, cells treated with RPh-Ac (0.01%; 0.2 mg/ml) were altered in shape, and developed thick, densely staining very long single protrusions reminiscent of neuronal cell axons. After 48 hour of incubation, cells treated with RPh-Ac (0.025%; 0.25 mg/ml) displayed a larger number of thinner long protrusions reminiscent of dendrites; and after 48 hours of incubation with RPh-Ac the thin long protrusions formed junctions with similar protrusions in adjacent cells creating a network of inter-connected cells, potentially capable of communicating information between one another (FIG. 11B). Similar networks occur normally between neurons in the central nervous system and enable transmission and processing of information.

While control cells proliferated during the 48 hour incubation period (FIG. 11C), RPh-Ac treated cells rapidly ceased to proliferate and the cells remained in sparse density, further supporting the notion of cell differentiation.

A Scoring System for the Potency in Inducing Cell Differentiation

On the basis of the above results, a scoring system was developed to evaluate the potency of the fractions for inducing differentiation in cell culture, with cells plated $2 \times 10^3$ per well. The grades and their respective descriptions are set out in Table 2.

TABLE 2

| Effect | Grade |
|---|---|
| Proliferation rate | High = 0 |
| | Medium = 1 |
| | Low = 2 |
| Cells are forming elongated protrusions | No = 0 |
| | protrusions = 1 |
| | neuron like = 2 |
| Neurites (neuron-like elongations)/ body ratio | ≤2 = 0 |
| | >2 ≤3 = 1 |
| | >3 = 4 |

TABLE 2-continued

| Effect | Grade |
|---|---|
| Percent of differentiated cells | ≤10% = 0 |
| | >10% ≤30% = 1 |
| | >30% ≤70% = 2 |
| | ≥70% = 3 |
| Clearly visible junctions between neurites and/or cell bodies | ≤30%, = 0 |
| | >30% <70%, = 1 |
| | ≥70% = 2 |
| Visible, clear synaptic-like buttons along the neurites and at the ends of the neurites | <30% = 0 |
| | >30% <50% = 1 |
| | ≥70% = 2 |

Figure 11C:
FIG. 11C shows the effect of the cottonseed oil vehicle on ARPE-19 cells.

The same assays were performed using the following treatments:

Cottonseed oil vehicle (negative control) (results shown in FIG. 11C)

Figure 12A:
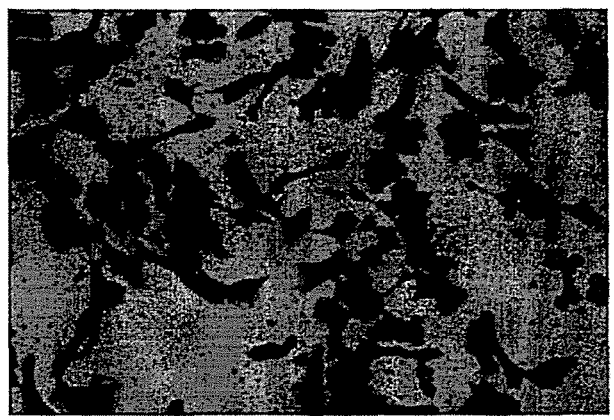
FIG. 12A shows the effect of the hexane-insoluble fraction isolated from the acidic fraction prepared according to the teaching of WO2003/097212 on ARPE-19 cells.

Acidic fraction according to WO2003/097212 and Hexane insoluble material isolated from acidic fraction according to the teaching of WO 2003/097212, 1% in ethanol (Results shown in FIG. 12A)

Figure 12B:
FIG. 12B shows the effect of 1% (w/w) ethanolic solution of the isolated acidic fraction prepared according Example 1 of the current invention on ARPE-19 cells.

RPh-Ac, 1% in ethanol (Results shown in FIG. 12B)

Figure 12C:
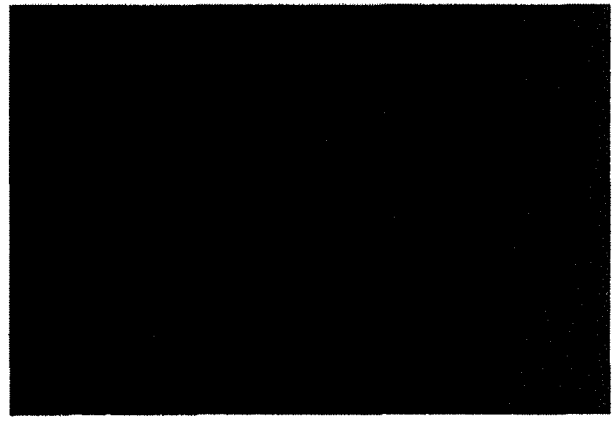
FIG. 12C shows the effect of the ethanol vehicle on ARPE-19 cells.

Ethanol vehicle (negative control) (Results shown in FIG. 12C).

Results according to the above scoring table for evaluating the differentiation observed in FIG. 11 and FIG. 12, in response to the various treatments, is depicted in Tables 3 and Table 4, below.

TABLE 3

| Name of fractions | Acidic WO 2003/092712 | | | | RPh-Ac | | | | Vehicle (cottonseed oil) | | | |
|---|---|---|---|---|---|---|---|---|---|---|---|---|
| Volume (ul) | 3.5 | 5 | 7 | 10 | 2 | 3.5 | 5 | 7 | 2 | 3.5 | 5 | 7 |
| Differentiation grade | 1 | 2 | 2 | 4** | 4 | 3 | 10 | _* | 0 | 0 | 0 | 0 |
| Differentiation score | 1 | 2 | 2 | 3** | 3 | 3 | 4 | _* | 0 | 0 | 0 | 0 |

*In these amounts the cells had reached full differentiation and subsequently died naturally before the end of the 48 hours incubation.
**Cells were clearly stressed and showed at best only hints of differentiation.

TABLE 4

| Name of fractions | Hexane insoluble Acidic WO2003/092712 (1% w/w in) ethanol | | | | RPh-Ac (1% w/w in ethanol) | | | | Vehicle (Ethanol) | | | |
|---|---|---|---|---|---|---|---|---|---|---|---|---|
| Volume (ul) | 3.5 | 5 | 7 | 10 | 2 | 3.5 | 5 | 7 | 2 | 3.5 | 5 | 7 |
| Differentiation grade | 1 | 1** | 2** | 2** | 4 | 3 | 15 | _* | 0 | 0 | 0 | 0 |
| Differentiation score | 1 | 1** | 2** | 2** | 3 | 3 | 5 | _* | 0 | 0 | 0 | 0 |

*In these amounts the cells had reached full differentiation and subsequently died naturally before the end of the 48 hours incubation.
**Cells were clearly stressed and showed only early hints of differentiation.

The cells were then washed 2× with PBS and fixed with 4% paraformaldehyde. To determine protein expression of, Synaptophysin, pAkt$^{Ser473}$, and phosph-GSK3-beta$^{Ser9}$ in the cells, the glass coverslips were stained with mouse/rabbit monoclonal antibodies direct against human Synaptophysin, pAkt$^{Ser473}$, and phosphor-GSK3-beta$^{Ser9}$, followed by secondary FITC-labeled anti-mouse/rabbit IgG. The cells nuclei were counter stained with DAPI. Test and control preparation were then evaluated in a fluorescence microscope. The results are presented in FIGS. 13A-C, herein below.

Figure 13A:
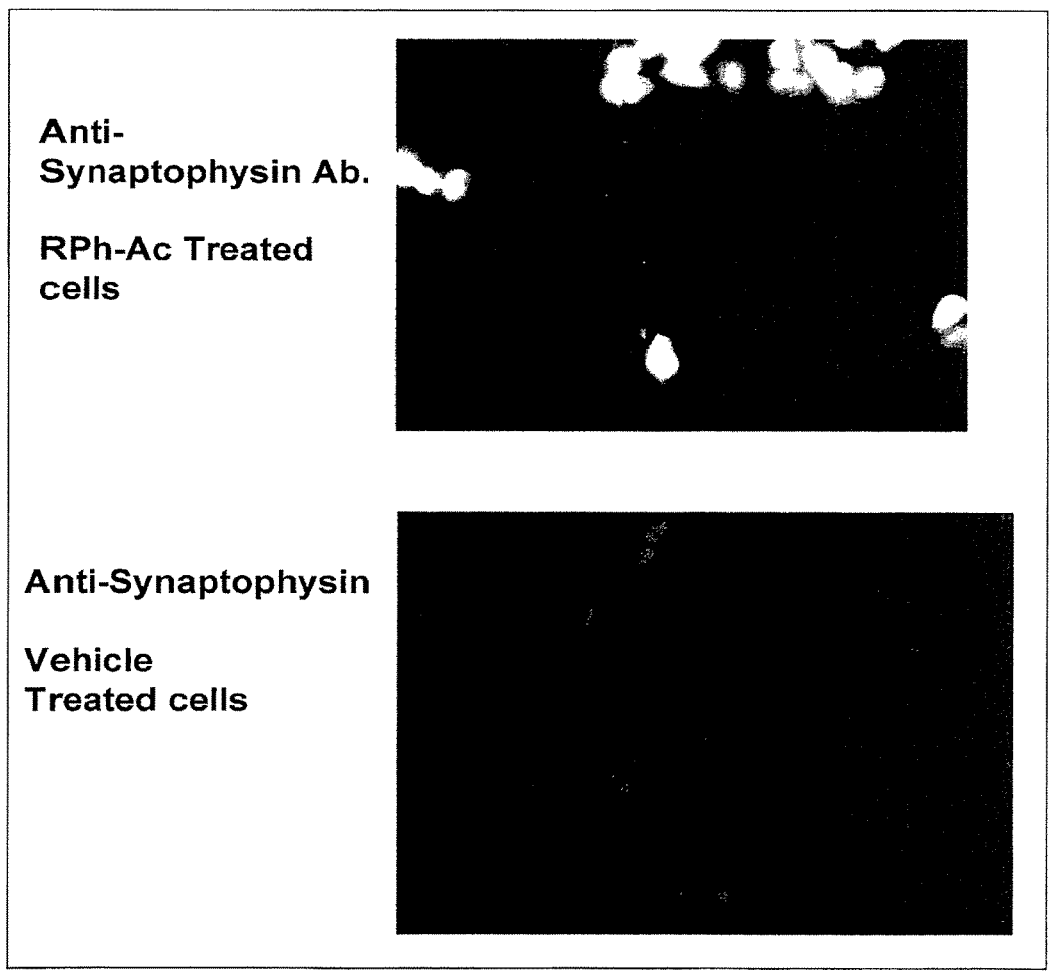
FIGS. 13A-C shows pictograms of cells treated with RPh-Ac (top panel) or non-treated cells (vehicle, bottom panel) and stained with antibodies (Ab.) to: Synaptophysin (FIG. 13A); phophorylated Akt (pAk$^{Ser473}$) (FIG. 13B); to phopshorylated GSK3-beta$^{Ser9}$ (FIG. 13C).

The results shown in FIG. 13A, demonstrate that in cells treated with the composition RPh-Ac, high levels of Synaptophysin clusters were evident in cellular processes (Top panel), as compared to control cells (bottom panel) where Synaptophysin is not expressed at all. Synaptophysin is an abundant synaptic vesicle in the brain and regulates activity-dependent synapse formation in neurons. Synaptophysin has been widely used to identify synapse formation in differentiating neuronal cells.

The activities of GSK-3 are negatively regulated by serine phosphorylation. Inactivation of GSK-3beta is a principal regulatory target of the phosphatidyl-inositol 3-kinase/Akt survival pathway and exert some of its neuroprotective effects. GSK-3 inactivation has been proposed as a mechanism to promote neuronal survival functions, including regulation of neurite formation and modulation of glutamatergic neurotransmission. GSK-3 beta inhibition has also been implicated in axonal morphology and synaptic protein clustering in developing neurons. Dysregulation of GSK-3-mediated substrate phosphorylation and signaling pathways has been implicated in the pathophysiological conditions of a variety of diseases, including Alzheimer disease, type 2 diabetes, and cancer schizophrenia and mood disorders.

Figure 13B:
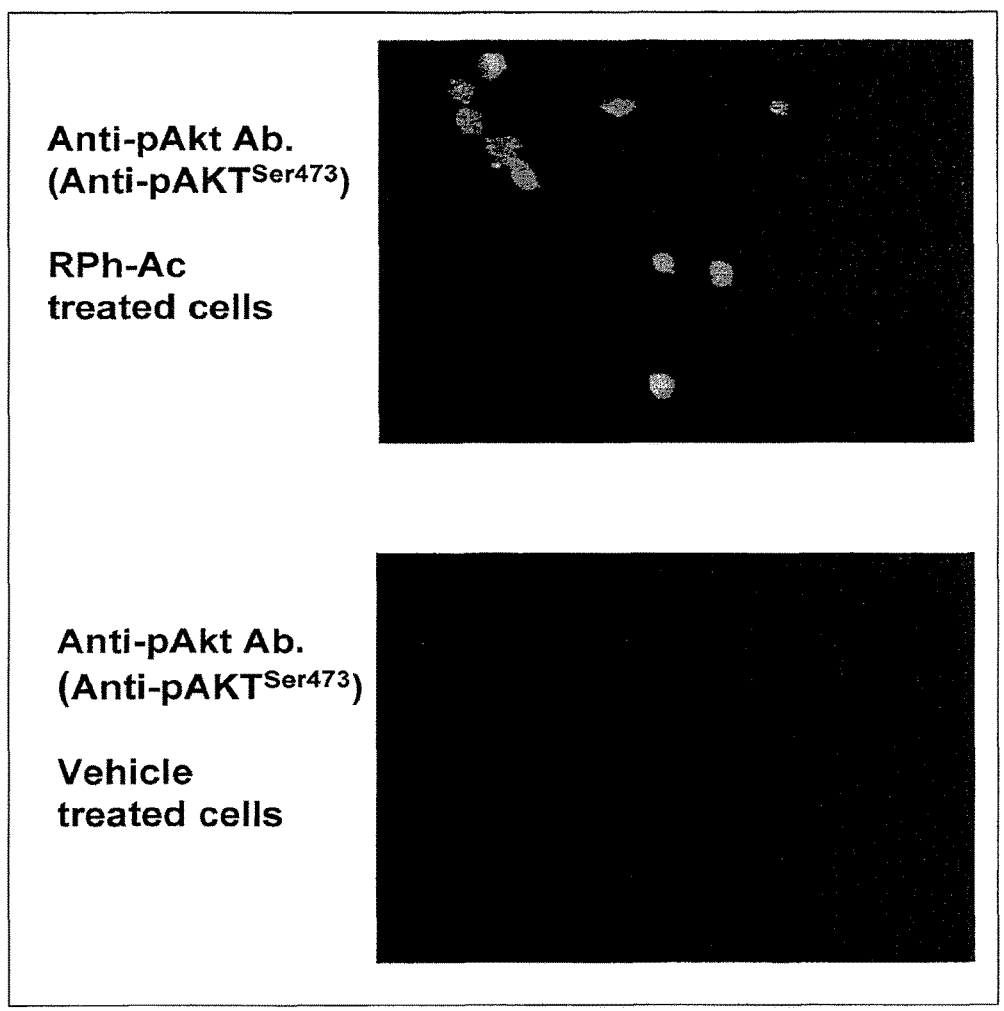
Figure 13C:
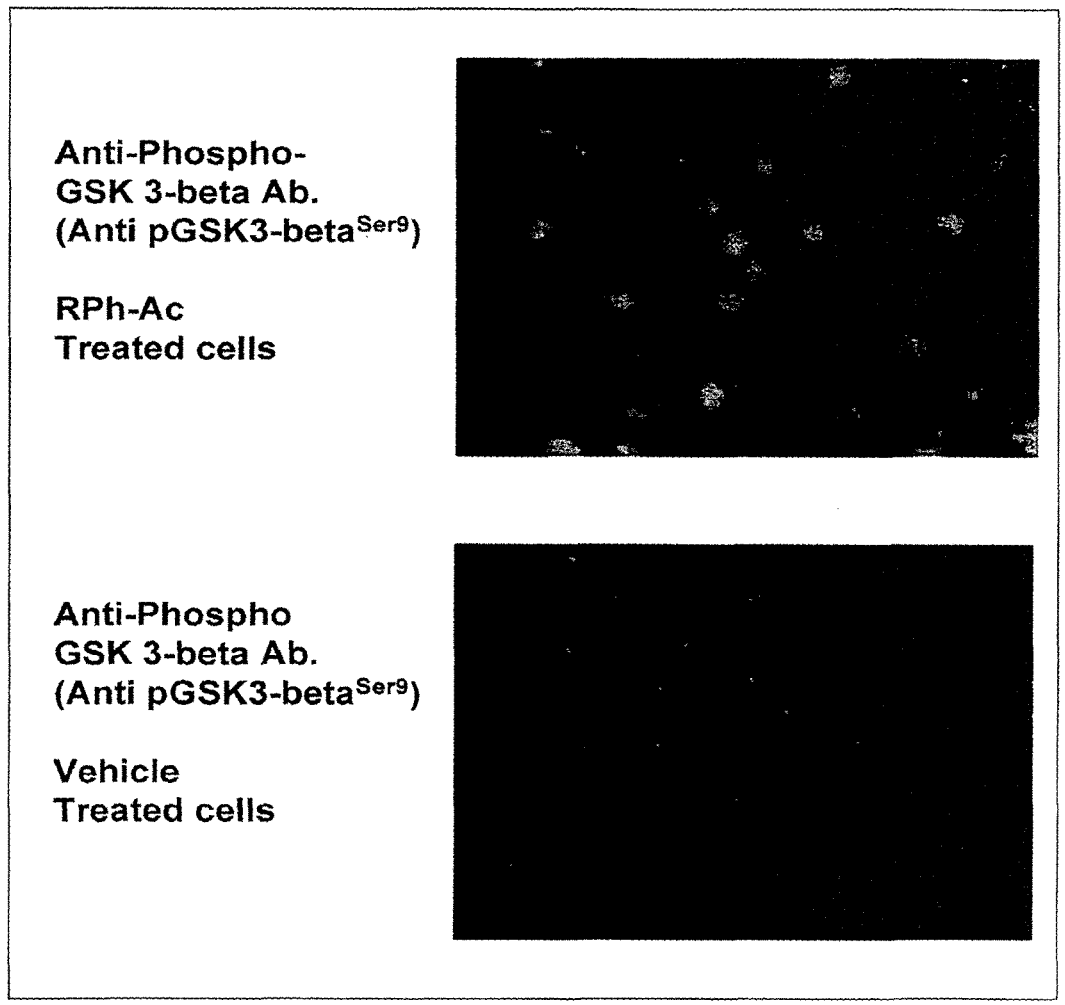

The results shown in FIG. 13B, demonstrate that cells treated with the composition RPh-Ac exhibit high levels of pAkt$^{Ser473}$ (Top panel), as compared to vehicle treated cells (bottom panel). The results shown in FIG. 13C, demonstrate that cells treated with the composition RPh-Ac exhibit high levels of pGSK-beta$^{Ser9}$ as well as changes in its localization, as compared to vehicle treated cells (bottom panel). These results suggest that composition RPh-Ac inactivates GSK3 beta by its phosphorylation on Ser9 through activation of Akt (phosphorylation of Ser 473).

Example 5. Synergistic Effect of Combinations of Specific Triterpenodis Compounds of the Isolated Acidic Fraction in Rat MCAO Model Stroke is a prominent cause of serious, long-term disability and the third leading cause of death in the United States. Ischemic strokes comprise over 88% of all strokes, making them the most common type of cerebrovascular injury. Ischemic conditions in the brain cause neuronal death, leading to permanent sensorimotor and cognitive deficits. The Middle Cerebral Artery occlusion (MCAO) model is a reliable model for stroke in rats and mimics the human condition. Occlusion of MCA leads to injury of the sensorimotor cortex due to neuronal loss. The level of this injury can be assessed by histology evaluation of the infarct size and various behavior tests. Behavioral improvement after stroke induction and low infarct volumes indicate a better pathological condition and are probably the result of either neuroprotection or neurogenesis. Therefore, the MCAO model can serve as reliable testing system to evaluate efficacy of drugs as a therapeutic agents for impaired neurological conditions, such as, for example, stroke and neurodegenerative diseases/conditions.

For the experiments described herein, the animals are anesthetized using ketamine/xylazine solution. The animal's neck is then shaved and a midline incision is made in the skin of the neck, and the tissue underneath is bluntly dissected. The right common carotid artery (CCA) and its junction with the external carotid artery (ECA) and internal carotid artery (ICA) are exposed by blunt dissection. The CCA is then transiently closed by positioning around it a 3-0 silk suture material. The ECA is permanently occluded with the same type of suture material. A third closure, transient, is also done in the ICA with 3-0 silk suture material.

A small hole is cut in the ECA and the nylon thread is inserted into the ICA while avoiding entrance into the pterygopalatine artery. The thread is inserted 21-25 mm until a slight resistance is felt. Then a 3-0 silk suture knot secures the thread.

Following surgery, the rats are returned to their cages and remain under a heating lamp until they awake.

Two parameters are monitored and recorded during the ischemic surgery procedure: animal's core temperature and blood glucose level (BGL).

Core temperature is monitored using rectal probe (YSI USA model 400) connected to a measuring unit (Cole Parmer model 8402-00) during the entire surgery period. Ischemic insult is started when rectal temperature is 37-38° C.

In view of the beneficial effect of RPh-Ac fraction composition on cells (as exemplified above herein), various compounds comprised within the RPh-Ac fraction were tested for their in-vivo effects.

Abbreviations used for the tested compounds and combinations:
OA: Oleanonic acid
MDA: Masticadienoic acid
IMDA: Isomasticadienoic acid The rats of the different groups were injected twice a week subcutaneous with 25 microliters of designated test item. First injection was given three hours after stroke induction. The following formulations were used as test items for injection:
Vehicle: cottonseed oil
IMDA: 0.65% (w/w) in cottonseed oil
MDA: 0.65% (w/w) in cottonseed oil
IMDA and MDA: each 0.65% (w/w) in cottonseed oil
IMDA, MDA and OA: each 0.65% (w/w) in cottonseed oil MDA alone; IMDA alone; a combination of MDA+IMDA; and a combination of OA+MDA+IMDA, were tested using a rat MCAO model, for their therapeutic capacity. Stroke induced rats were treated with each of the tested compounds and the improvement of their sensorimotor abilities were tested using the adhesive removal test. In this test, a small adhesive tape is attached to the front paws of the rats and serves as a tactile stimulus. The time to remove the tape is recorded. The adhesive removal tape was conducted before the induction of stroke, to evaluate the base line time of each group and at 27 days after the injury, following twice a week injections of the test items.

Figure 14A:
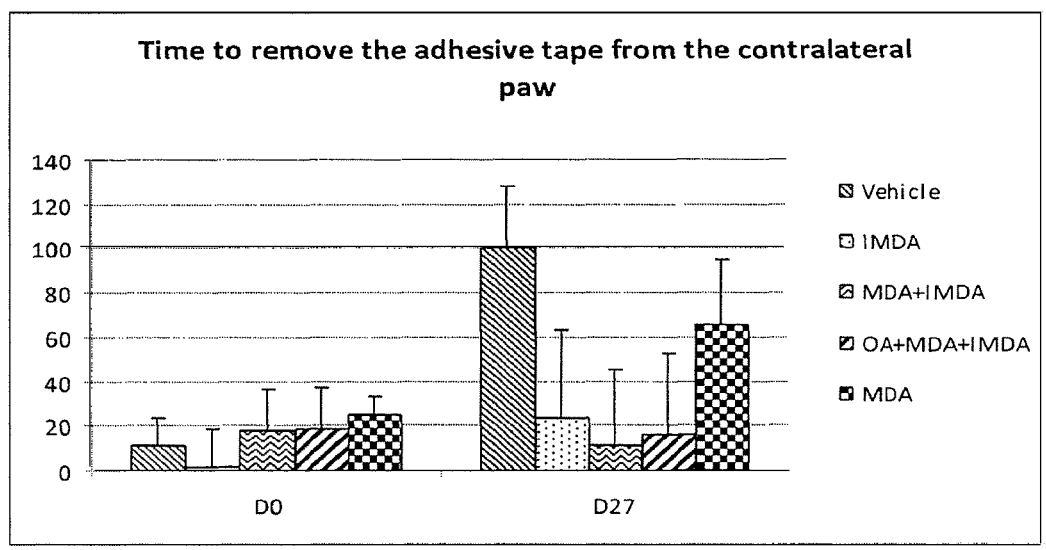
FIG. 14A shows graphs depicting the results of the rat MCAO model with respect to removal time of adhesive tape from the contralateral paw for different compositions of the current invention.

Results:
As shown in the graphs of FIG. 14A, which show the time (in seconds) it took the rats to remove the adhesive tape from the contralateral paw, IMDA alone, was able to improve the score of treated rats in the adhesive removal test, compared to vehicle treated rats. MDA alone was only slightly better than the vehicle control. However, the combination of IMDA+MDA or OA+MDA+IMDA (right thick diagonal line), clearly improved the efficacy of the treatment and the animals were back to their base line (day 0, D0) performance on day 27 (D27).

Figure 14B:
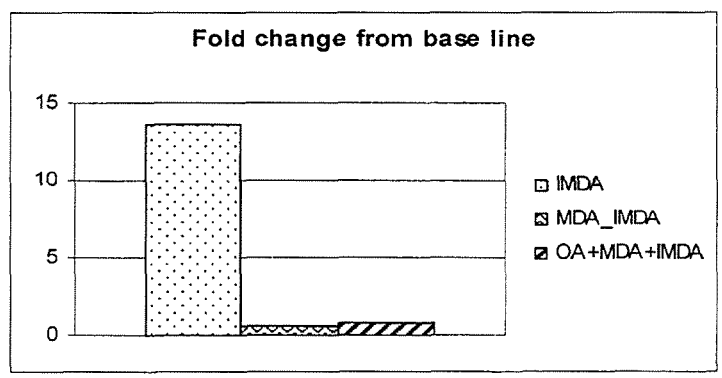
FIG. 14B shows graphs depicting the baseline fold change by the compositions: Isomasticadienoic acid (IMDA), or a combination of Isomasticadienoic acid and Masticadienoic acid (IMDA+MDA); or combination of Oleanonic acid, Isomasticadienoic acid and Masticadienoic (OA+MDA+IMDA), on the removal of adhesive tape from the contralateral paw.

Since IMDA by itself almost restored the base line score of the rats, the ratio of the beneficial test items relative to the base line was analyzed. As shown in FIG. 14B, IMDA, which significantly improved the rat's sensorimotor condition, was still 10 fold worse than the base line score. This suggests that IMDA by itself is limited in its effect and cannot fully restore the base line sensorimotor function. However, surprisingly, the combinations of IMDA and MDA or the combination of IMDA, MDA and OA further increased efficacy, resulting in dramatic improvement of the sensory-motor capacity to a level even lower than the recorded baseline. These results demonstrate clearly the strong synergistic effect of the combinations of IMDA, MDA and OA.

The results presented herein strongly support the therapeutic potential of combination of isomaticadienoic acid and masticadienoic acid or the combination of isomasticadienoic acid, masticadienoic acid and oleanonic acid, and indicate a strong synergistic effect of these compounds on each other with respect to treatment of impaired neurological function and regeneration of neuronal tissue.

Example 6. Wound Healing in Rats

Figure 15:
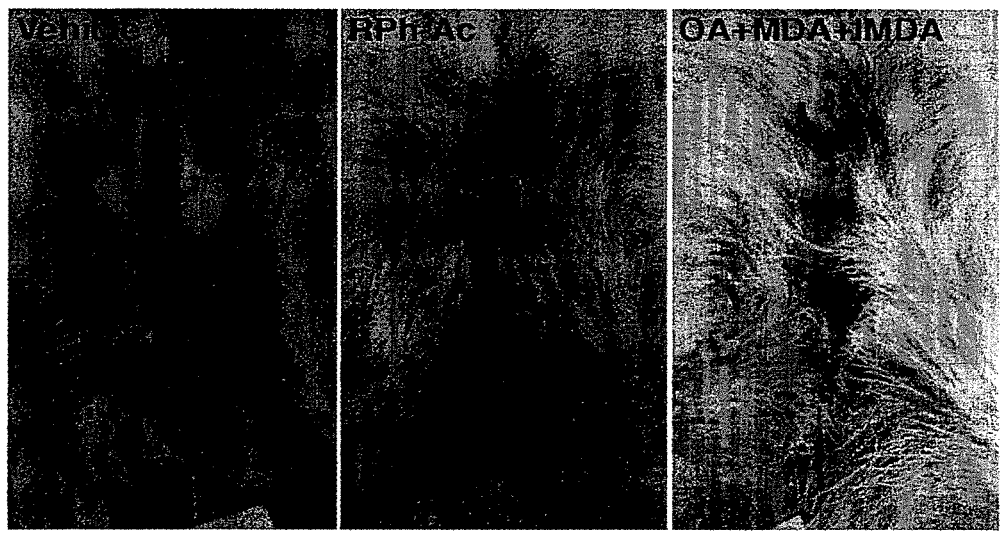
FIG. 15 shows pictographs of rats demonstrating the effect of cottonseed vehicle (left hand panel), RPh-Ac (middle panel) and the combination of OA+MDA+IMDA (right hand panel) on the healing of surgical wounds in rats from the MCAo model of Example 5.

For the rats used in the MCAo model of Example 5, the healing of the surgical wounds was used as an indicator for the wound healing potential of the tested formulations used in Example 5.
The pictograms shown in FIG. 15 were taken of wounds during day 7 of the MCAO model, for rats treated with vehicle (plain cottonseed oil, Left Panel), RPh-Ac (middle panel) and the mixture of oleanonic acid, masticadienoic acid and isomasticadienoic acid (right). The photographs clearly indicate that the wounds of animals treated with RPh-Ac (middle panel) or with the mixture of oleanonic acid, masticadienoic acid and isomasticadienoic acid (right panel) are in a more advanced stage of healing in comparison with the wound of the vehicle treated animal.

Example 7. Preparation of Complexes of Cyclodextrin

Cyclodextrins, by virtue of their ability to form inclusion complexes with many drugs, can substantially increase the aqueous solubility of biopharmaceuticals, in particular those that are defined as water-insoluble such as particular terpenoid compounds. Cyclodextrins are water-soluble compounds, which can form reversible complexes with poorly water-soluble molecules resulting in a soluble molecular inclusion complex. When the inclusion complex of the drug-cyclodextrin combination is diluted in a sufficiently large volume of water or blood, it dissociates rapidly, releasing the sequestered pharmacologically active agent.

Complexation of isolated acidic fractions described herein with β-HPCD will be performed as follows:
a. Dissolution of pre weighed gum mastic fraction in a minimum amount of non-polar solvent such as hexane, heptane, or the like.
b. Dropwise addition of the non-polar solvent to the β-HPCD powder.
c. Drying at 50-80° C. until non-polar solvent evaporates.
d. Mixing with necessary amount of water.
e. Dissolution with sonication and heating.
f. Filtration through 0.2-0.45 μm filter.

Example 8. Preparation of Nanoemulsions of Isolated Acidic Fraction of Mastic Gum Liquid oil-in-water nanoemulsion formulations are to be prepared by high pressure emulsification techniques of all lipid ingredients and the active component dissolved in the lipid oil phase and emulsified with an aqueous phase, projected to result in the formation of stable, spheric and uniformly dispersed drug-containing lipid nanodroplets. The emulsion droplet size reduction is essential to generate drug formulations with high stability. Preferred nanoemulsion droplets have a mean droplet size of less than one micron (generally in the range of 0.1-0.2 μm) uniformly dispersed in an aqueous phase. The uniqueness of the large internal hydrophobic oil core of the nanoemulsion droplets provides high solubilization capacity for water insoluble compounds.

1. Preparation of Oil Phase

The oil phase is composed of 13% lipoid E-75, 0.026% αTP-succinate, propylparaben as antioxidant and 86.9% Miglyolo 810. Gum mastic fraction prepared as in Example 1 is dissolved in the oil phase. The components are mixed with mild heating until a homogenous completely solubilized solution is obtained.

2. Preparation of Aqueous Phase

The aqueous phase is composed of 0.1% EDTA, 0.5% Tween-80, 2.3% glycerol, methylparaben as preservative and 97.1% water. pH was adjusted to 7.4 by NaOH 1N.

3. Mixing of Oil and Aqueous Phases

Oil phase (3.7 g) is heated and added to 70 ml of the aqueous phase (preheated). The mixture is gently stirred for 10-15 min at room temperature.

4. Preparation of Oil-in-Water Coarse Emulsion

An oil-in-water emulsion is prepared using the medium size dispenser and high shear homogenizing unit Polytron®, at 20,000 rpm for 5 min.

5. Sizing the Emulsion to Submicron Range by Gaulin® High Pressure Homogenizer

The droplet size of the emulsion obtained after step 4 is reduced to the submicron (nanosize) range by submitting the emulsion to high shear homogenization using the Gaulin® Microlab 70 high pressure homogenizer at 800 bar pressure. A total of 5-6 cycles should be performed to obtain homogenous nanoemulsion droplets having average particle size of less than 200 nm. Particle size is to be determined by photon correlation spectroscopy (PCS) using a N4MD particle size analyzer (Coulter® Electronics, UK). When most of the particles (>90%) are smaller than 200 nm, the sizing process is determined to be complete.

6. Sterile Filtration

Filtration at aseptic conditions of the nanoemulsion to sterile vials using a 0.2 μm PES sterile filter and storage at 40° C.

Example 9. Preparation of Spray-Dried Powder

A convenient process for manufacturing the gum mastic fraction-lipid mixture product is by direct spray-drying of the formulation from a mixture of non-polar solvent dispersion containing all the lipid ingredients and water containing the hydrophilic components, taking into account cost effectiveness and upscaling considerations. The selected spray-drying method is optimized in order to get a fine, free-flowing powder. The gum mastic fraction is to be dissolved in the lipid phase containing the lipid ingredients lecithin, tricaprin (capric acid triglyceride), tocopherol succinate and warmed (~40° C.) in a non-polar solvent until a good dispersion is obtained. A dispersion of fumed silicon dioxide (Cab-O-Sil®) in water (5%) will be prepared by swelling the powder in purified water. The resultant slurry (prewarmed to 40° C.) may then be poured slowly into the non-polar solvent lipid dispersion and the mixture agitated at 40° C. for about 1 hr until a homogenous dispersion is obtained. The mixture is then to be spray-dried using the Yamato Pulvis® GA32 spray-dryer. Typical spray-drying conditions are: flow rate 7 ml/min, inlet temperature 130° C., outlet temperature 70° C., and drying air flow 0.5 m$^3$/min. A homogeneous dry powder containing the gum mastic fraction-lipid mixture is expected to be obtained.

The gum mastic fraction-lipid mixture formulation prepared by the direct spray drying process is expected to show good water dispersibility, thus being suitable for the preparation of solid-dosage forms such as hard gelatin capsules or tablets for enhanced oral delivery with good oral bioavailability.

Example 10. Preparation of Liposomal Preparations

Lipids containing dissolved isolated acidic fraction of mastic gum are to be dissolved in 100 ml dichloromethane in a round bottom flask, and stirred for 30 min at room temperature until a clear transparent solution is obtained. Solvent will be evaporated using a rotary evaporation unit at 39° C. Typical conditions include rotation of the flask at 4.5 rpm, 5 min under atmospheric pressure, followed by 10-30 min (until full evaporation of the solvent) under weak vacuum, and finally 15 min under full vacuum. At the end of the evaporation process a uniform lipid film will be created. The lipid film will be dissolved in 15 ml isotonic buffer. Liposomes are prepared by vigorous shaking for 10-30 min using multi-wrist shaker, until a uniform and milky dispersion of multilamellar vehicle (MLV) is formed and no remaining lipid film remains apparent. In order to obtain an equilibrated and homogenous liposome preparation, the flask may be further shaken at 37° C. for 30-90 min. at 270 rpm.

Example 11. Preparation of Microemulsions Containing Isolated Acidic Fraction of Mastic Gum Several surfactants commonly used in parenterals may be utilized to develop water-in-oil and oil-in-water-microemulsions acceptable for injectable, oral and topical use. Pharmaceutically acceptable surfactants suitable for the formation of microemulsion formulations include non-ionic surfactants including polyoxyl 40 hydrogenated castor oil (sold under the trade name Cremophor RH40®), polyoxyl 35 castor oil (sold under the trade name Cremophor® EL), polyoxyethylene sorbitan fatty acid esters (polysorbates), poloxamers (Pluronics®), vitamin E-TPGS 1,000 (VE-TPGS 1,000), polyoxyethylene alkyl ethers, Solutol® HS-15, Tagat® TO, Peglicol 6-oleate, polyoxyethylene sterates, or saturated polyglycolyzed glycerides, all of which are commercially available. The preferred surfactants include polyoxyl 40 hydrogenated castor oil (Cremophor® RH40®), polyoxyl 35 hydrogenated castor oil (Cremophor® EL), polyoxyethylene sorbitan fatty acid esters (polysorbates), poloxamers (Pluronics®), and vitamin E-TPGS 1,000. The total amount of the surfactant present in the composition will be generally from about 100 to about 700 mg/g, and preferably from about 300 to about 500 mg/g.

Preparation of microemulsions containing the isolated acidic fraction may be performed by dissolving the isolated acidic fraction in an appropriate amount of oil such as medium chain tryglycerides (Miglyol) in a suitable vial. The vial is then capped. The vial is put into a water bath of about 50-60° C. and shaken gently until all of the drug material is completely dissolved. After the vial is cooled to room temperature, an appropriate amount of surfactant (such as Cremophor® EL or VE-TPGS) is added and followed by the mixture of mono- and di-glycerides of fatty acids, if any. The vial is then capped and placed into the water bath of about 50-60° C. The vial is shaken gently to obtain a clear, uniform solution. This solution can be filled into HPMC capsules and stored at room temperature before oral dosing. Alternatively, the substituted polymer powders (such as HPMC) can be added into the solution with adequate agitation (i.e., stirring, shaking) to obtain a uniform polymer suspension. The resulting composition can then be filled into either soft gelatin or hard gelatin capsules and stored at room temperature before oral dosing. Alternatively the microemulsion formulation can be used as a topically or filtered through 0.2 um membranes to be administered parenterally.

The microemulsions have good water-dispersibility properties and self-emulsify when diluted in aqueous media to form small nanometric micelles that with enhanced bioavailability.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for inducing differentiation of undifferentiated cells into neural cells, the method comprising administering to the undifferentiated cells a composition consisting of a mixture of triterpenoids comprising at least two triterpenoic acids selected from the group consisting of: masticadienonic acid, isomasticadienonic acid, oleanonic acid; moronic acid, 3-O-acetyl masticadienolic acid; 3-O-acetyl isomasticadienolic acid; and a pharmaceutically acceptable carrier; wherein the suitable cells are selected from the group consisting of ectodermal cells, mesodermal cells, endodermal cells and stem cells of said lineages.

2. The method according to claim 1, wherein the ectodermal cells are selected from neuronal cells and their corresponding stem cells.

3. The method according to claim 1, wherein the mesodermal cells are selected from endothelial cells and their corresponding stem cells.

4. The method according to claim 1, wherein the ectodermal and endodermal cells are selected from epithelial cells and their corresponding stem cells.

5. The method according to claim 1, wherein the triterpenoic acids are masticadienonic acid and isomasticadienonic acid.

6. The method according to claim 1, wherein the triterpenoic acids are masticadienonic acid, isomasticadienonic acid and oleanonic acid.

7. The method according to claim 1, wherein the triterpenoids are masticadienonic acid, isomasticadienonic acid, oleanonic acid; moronic acid, 3-O-acetyl masticadienolic acid and 3-O-acetyl isomasticadienolic acid.

8. The method according to claim 1, wherein the composition is administered to undifferentiated cells in vivo by a route selected from the group consisting of oral, topical, parenteral, intramuscular, subcutaneous, intradermal, vaginal, rectal, intracranial, intranasal, intraocular, auricular, pulmonary intralesional, intraperitoneal, intraarterial, intracerebral, intracerebroventricular, intraosseus and intrathecal.

9. The method according to claim 1, wherein the undifferentiated cells are contacted in vitro or ex vivo and are implanted or transplanted into a subject.

10. The method of claim 1, wherein the administration to undifferentiated cells is carried out in vivo.

11. The method of claim 1, wherein the administration to undifferentiated cells is carried out ex vivo.

12. The method of claim 1, wherein the administration to undifferentiated cells is carried out in vitro.

* * * * *